US008437865B2

(12) United States Patent
Dabney et al.

(10) Patent No.: US 8,437,865 B2
(45) Date of Patent: May 7, 2013

(54) SHIELDED NETWORK FOR AN ACTIVE MEDICAL DEVICE IMPLANTABLE LEAD

(75) Inventors: Warren S. Dabney, Orchard Park, NY (US); Robert Shawn Johnson, North Tonawanda, NY (US); Holly Noelle Mosciano, Lancaster, NY (US); Robert A. Stevenson, Canyon Country, CA (US); Henry R. Halperin, Pikesville, MD (US); Albert C. Lardo, Baltimore, MD (US); Kishore Kumar Kondabatni, Williamsville, NY (US)

(73) Assignee: Greatbatch Ltd., Clarence, NY (US)

( * ) Notice: Subject to any disclaimer, the term of this patent is extended or adjusted under 35 U.S.C. 154(b) by 348 days.

(21) Appl. No.: 12/891,292

(22) Filed: Sep. 27, 2010

(65) Prior Publication Data

US 2011/0054582 A1    Mar. 3, 2011

Related U.S. Application Data

(63) Continuation-in-part of application No. 12/873,862, filed on Sep. 1, 2010, which is a continuation-in-part of application No. 12/607,234, filed on Oct. 28, 2009, now Pat. No. 8,175,700, which is a continuation-in-part of application No. 12/407,402, filed on Mar. 19, 2009, now Pat. No. 8,195,295, which is a continuation-in-part of application No. 11/558,349, filed on Nov. 9, 2006, now Pat. No. 7,945,322, application No. 12/891,292, which is a continuation-in-part of application No. 12/707,084, filed on Feb. 17, 2010, which is a continuation-in-part of application No. 10/123,534, filed on Apr. 15, 2002, now Pat. No. 7,844,319, application No. 12/891,292, which is a continuation-in-part of application No. 12/686,137, filed on Jan. 12, 2010.

(60) Provisional application No. 60/283,725, filed on Apr. 13, 2001, provisional application No. 61/149,833, filed on Feb. 4, 2009, provisional application No. 61/144,102, filed on Jan. 12, 2009.

(51) Int. Cl.
*A61N 1/00* (2006.01)
(52) U.S. Cl.
USPC .......................................................... 607/116
(58) Field of Classification Search .................... 607/116
See application file for complete search history.

(56) References Cited

U.S. PATENT DOCUMENTS

| 5,970,604 | A | 10/1999 | Person et al. |
| 6,669,909 | B2 * | 12/2003 | Shvets et al. ................... 422/502 |
| 6,900,708 | B2 * | 5/2005 | White et al. ................... 333/185 |
| 7,511,921 | B2 | 3/2009 | Mallary et al. |
| 7,689,288 | B2 | 3/2010 | Stevenson et al. |
| 2009/0243756 | A1 | 10/2009 | Stevenson et al. |
| 2010/0023000 | A1 | 1/2010 | Stevenson et al. |
| 2010/0100164 | A1 | 4/2010 | Johnson et al. |
| 2010/0160997 | A1 | 6/2010 | Johnson et al. |

* cited by examiner

*Primary Examiner* — George Manuel
(74) *Attorney, Agent, or Firm* — Michael F. Scalise

(57) ABSTRACT

A shielded component or network for an active medical device (AMD) implantable lead includes (1) an implantable lead having a length extending from a proximal end to a distal end, all external of an AMD housing, (2) a passive component or network disposed somewhere along the length of the implantable lead, the passive component or network including at least one inductive component having a first inductive value, and (3) an electromagnetic shield substantially surrounding the inductive component or the passive network. The first inductive value of the inductive component is adjusted to a account for a shift in its inductance to a second inductive value when shielded.

53 Claims, 30 Drawing Sheets

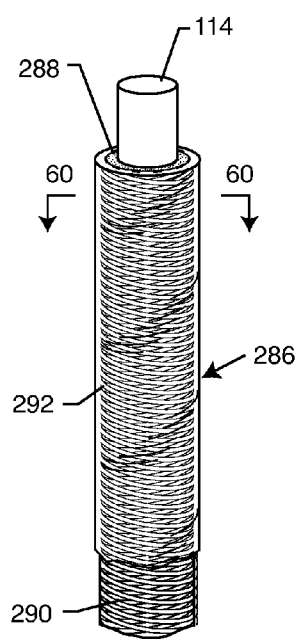
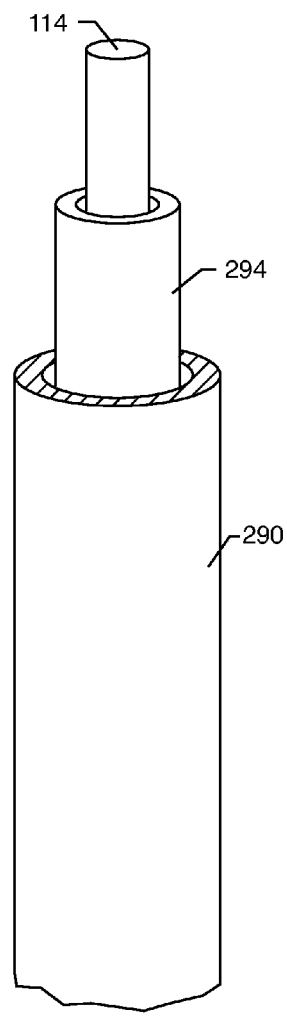
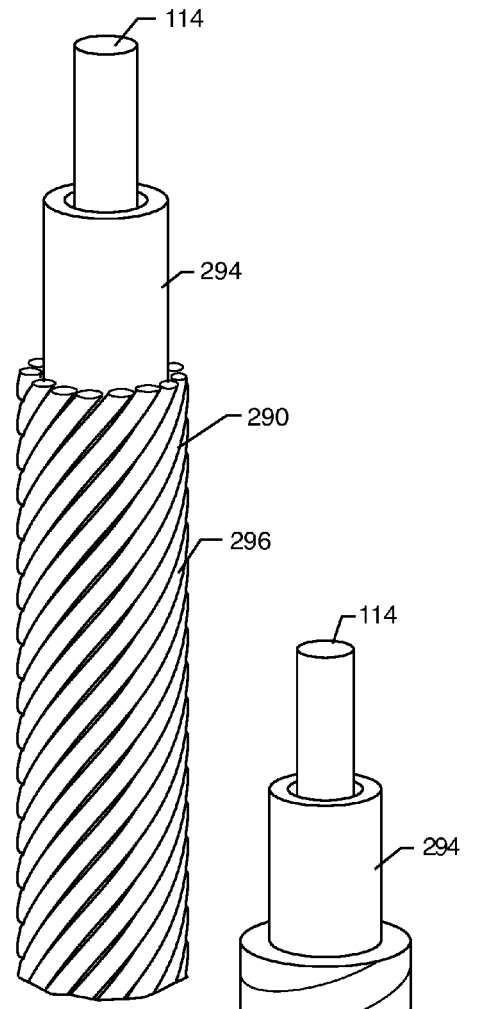
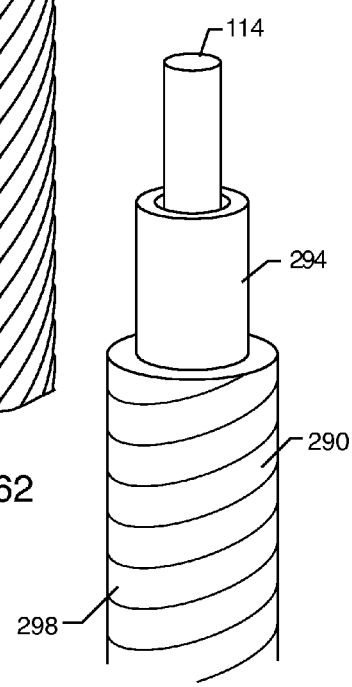
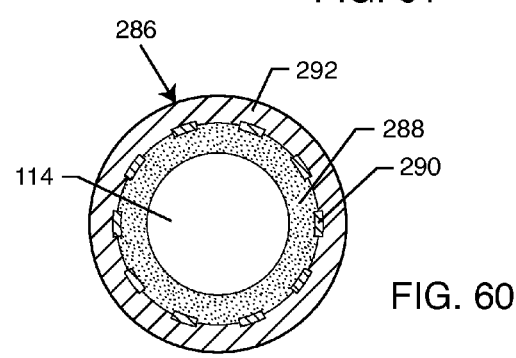
FIG. 59
FIG. 60
FIG. 61
FIG. 62
FIG. 63

SHIELDED NETWORK FOR AN ACTIVE MEDICAL DEVICE IMPLANTABLE LEAD

FIELD OF THE INVENTION

This invention generally relates to the problem of high frequency energy induced onto implanted leads during medical diagnostic procedures such as magnetic resonant imaging (MRI). More specifically, the present invention relates to an implantable medical system comprised of an active medical device (AMD) and at least one lead extending exteriorly from a proximal end at or adjacent to the AMD, to a biological sensing or stimulating electrode at a distal end. The lead has a passive component or network, including at least one inductive component disposed somewhere along its length between the proximal end and distal end. At least the inductive component of the passive component or network is electromagnetically shielded.

BACKGROUND OF THE INVENTION

The radio frequency (RF) pulsed field of MRI can couple to an implanted lead in such a way that electromagnetic forces (EMFs) are induced in the lead. The amount of energy that is induced is related to a number of complex factors, but in general, is dependent upon the local electric field that is tangent to the lead and the integral of the electric field strength along the lead. In certain situations, these EMFs can cause currents to flow into distal electrodes or in the electrode interface with body tissue. It has been documented that when this current becomes excessive, overheating of said lead or its associated electrode or overheating of the associated interface with body tissue can occur. There have been cases of damage to such body tissue which has resulted in loss of capture of cardiac pacemaking pulses or tissue damage severe enough to result in brain damage or multiple amputations, and the like.

Electromagnetic interference (EMI) is also a significant issue. It has been well demonstrated through various incidents and publications that an implanted lead can act as an antenna and pick up unwanted signals from the patient environment. In the past, there have been problems with microwave ovens, cell phones, and the like. Stray signals that are picked up on implanted leads can be coupled to the interior of the AMD and interfere with sensitive electronic circuits. In cardiac pacemakers, instances of EMI being detected as normal cardiac rhythms have resulted in pacemaker inhibition which can be life-threatening.

Magnetic resonance imaging (MRI) is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AMDs after an MRI procedure, sometimes occurring many days later. Moreover, there are a number of papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI unit. The first type is the main static magnetic field designated $B_0$ which is used to align protons in body tissue. The field strength varies from 0.5 to 3.0 Tesla in most of the commonly available MRI units in clinical use. Some of the newer research MRI system fields can go as high as 11.7 Tesla.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of 21 MHz to 64 MHz to 128 MHz depending upon the static magnetic field strength. The frequency of the RF pulse for hydrogen scans varies by the Lamour equation with the field strength of the main static field where: RF PULSED FREQUENCY in MHz=(42.56) (STATIC FIELD STRENGTH IN TESLA). There are also phosphorous and other types of scanners wherein the Lamour equation would be different.

The third type of electromagnetic field is the time-varying magnetic gradient fields designated $B_X$, $B_Y$, $B_Z$, which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur.

The cause of heating in an MRI environment is twofold: (a) RF field coupling to the lead can occur which induces significant local heating; and (b) currents induced between the distal tip and tissue during MRI RF pulse transmission sequences can cause local Ohms Law heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing capture threshold (PCT), venous ablation, Larynx or esophageal ablation, myocardial perforation and lead penetration, or even arrhythmias caused by scar tissue. Such long term heating effects of MRI have not been well studied yet for all types of AMD lead geometries. There can also be localized heating problems associated with various types of electrodes in addition to tip electrodes. This includes ring electrodes or pad electrodes. Ring electrodes are commonly used with a wide variety of abandoned implanted device leads including cardiac pacemakers, and neurostimulators, and the like. Pad electrodes are very common in neurostimulator applications. For example, spinal cord stimulators or deep brain stimulators can include a plurality of pad electrodes to make contact with nerve tissue. A good example of this also occurs in a cochlear implant. In a typical cochlear implant there would be sixteen pad electrodes placed up into the cochlea. Several of these pad electrodes make contact with auditory nerves.

Variations in the pacemaker lead length and implant trajectory can significantly affect how much heat is generated. A paper entitled, HEATING AROUND INTRAVASCULAR GUIDEWIRES BY RESONATING RF WAVES by Konings, et al., journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the leads of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar, multipolar and the like. It is very important that excessive RF current not flow at the interface between the lead distal tip electrode or electrodes and body tissue. In a typical cardiac pacemaker, for example, the distal tip electrode can be passive or of a screw-in helix type as will be more fully described. In any event, it is very important that excessive RF current not flow at this junction between the distal tip electrode and, for example, into surrounding cardiac or nerve tissue. Excessive current at the distal electrode to tissue interface can cause excessive heating to the point where tissue ablation or even perforation can occur. This can be life-threatening for cardiac patients. For neurostimulator patients, such as deep brain stimulator patients, thermal injury can cause permanent disability or even be life threatening. Similar issues exist for spinal cord stimulator patients, cochlear implant patients and the like.

A very important and possibly life-saving solution is to be able to control overheating of implanted leads during an MRI procedure. A novel and very effective approach to this is to first install parallel resonant inductor and capacitor bandstop filters at or near the distal electrode of implanted leads. For cardiac pacemaker, these are typically known as the tip and ring electrodes. One is referred to U.S. Pat. No. 7,363,090; US 2007/0112398 A1; US 2008/0071313 A1; US 2008/0049376 A1; US 2008/0024912 A1; US 2008/0132987 A1; and US 2008/0116997 A1, the contents of all of which are incorporated herein. US 2007/0112398 A1 relates generally to L-C bandstop filter assemblies, particularly of the type used in active implantable medical devices (AIMDs) such as cardiac pacemakers, cardioverter defibrillators, neurostimulators and the like, which raise the impedance of internal electronic or related wiring components of the medical device at selected frequencies in order to reduce or eliminate currents induced from undesirable electromagnetic interference (EMI) signals.

Other types of component networks may also be used in implantable leads to raise their impedance at MRI frequencies. For example, a series inductor may be used as a single element low pass filter. The inductance will tend to look like a high impedance at high frequencies, such as the RF pulsed frequencies of a typical MRI scanner. For more information on this refer to U.S. Pat. No. 5,217,010 (Tsitlik et al.), the contents of which are incorporated herein by reference.

U.S. Pat. No. 7,363,090 and US 2007/0112398 A1 show resonant L-C bandstop filters placed at the distal tip and/or at various locations along the medical device leads or circuits. These L-C bandstop filters inhibit or prevent current from circulating at selected frequencies of the medical therapeutic device. For example, for an MRI system operating at 1.5 Tesla, the pulsed RF frequency is 63.84 MHz, as described by the Lamour Equation for hydrogen. The L-C bandstop filter can be designed to resonate at or near 63.84 MHz and thus create a high impedance (ideally an open circuit) in the lead system at that selected frequency. For example, the L-C bandstop filter when placed at the distal tip electrode of a pacemaker lead will significantly reduce RF currents from flowing through the distal tip electrode and into body tissue. The L-C bandstop filter also reduces EMI from flowing in the leads of a pacemaker thereby providing added EMI protection to sensitive electronic circuits. In general, the problem associated with implanted leads is minimized when there is a bandstop filter placed at or adjacent to its distal tip electrodes.

At high RF frequencies, an implanted lead acts very much as like an antenna and a transmission line. An inductance element disposed in the lead will change its transmission line characteristics. The inductance can act as its own antenna pick-up mechanism in the lead and therefore, ideally, should be shielded. When one creates a very high impedance at the distal electrode to tissue interface by installation of a resonant bandstop filter as described in U.S. Pat. No. 7,038,900 and as further described in US 2007/0112398 A1, there is created an almost open circuit which is the equivalent of an unterminated transmission line. This causes a reflection of MRI induced RF energy back towards the proximal end where the AIMD (for example, a pacemaker) is connected. In order to completely control the induced energy in an implanted lead, one must take a system approach. In particular, a methodology is needed whereby energy can be dissipated from the lead system at the proximal end in a way that does not cause overheating either at the distal electrode interface or at the proximal end cap. Maximizing energy transfer from an implanted lead is more thoroughly described in US 2010/0160997 A1, the contents of which are incorporated herein by reference.

Accordingly, there is a need for attenuating the RF energy that can be induced onto or into an implanted lead system. Further, there is a need to provide shielding of passive network components, including any inductors that would be disposed along the length of the lead. Such shielding should reduce or prevent external electromagnetic fields from coupling RF electromagnetic energy to said passive component or network and, in particular, its inductive component(s). The present invention fulfills these needs and provides other related advantages.

SUMMARY OF THE INVENTION

The present invention resides in a shielded component or network for an active medical device (AMD) implantable lead, comprising: (1) an implantable lead having a length extending from a proximal end to a distal end, all external of an AMD housing, (2) a passive component or network disposed somewhere along the length of implantable lead, the passive component or network including at least one inductive component having a first inductive value, and (3) an electromagnetic shield substantially surrounding the inductive component or the passive network. The first inductive value of the inductive component is adjusted to account for a shift in its inductance to a second inductive value when shielded.

The passive component network may include at least one capacitive component electrically connected in parallel with the at least one inductive component to form a bandstop filter. The inductive component may comprise a solenoid inductor or a chip inductor, and the capacitive component may comprise a chip capacitor, parasitic capacitance, or a feedthrough capacitor. In this regard, the capacitive component may comprise parasitic capacitance formed between coils of the inductive component and/or between the inductive component and the electromagnetic shield. In a preferred embodiment, a dielectric material is disposed between coils of the inductive component and between the inductive component and the electromagnetic shield to facilitate formation of the parasitic capacitance. The capacitive component and the inductive component may form a parallel resonant bandstop filter and are tuned to impede induced current flow through the implantable lead at a selected center frequency or range of frequencies, typically comprising an MRI RF pulsed frequency or range of RF pulsed frequencies. The MRI RF pulsed frequency range includes tens of kilohertz, hundreds of kilohertz or megahertz.

A non-conductive insulator or dielectric material may be disposed between the passive component network and the electromagnetic shield.

In a preferred embodiment, an inductor is provided having first and second conductive terminals in spaced non-conductive relation, and a capacitor is also provided having first and second conductive terminals in spaced non-conductive relation. The inductor and the capacitor are physically disposed in series relative to one another, and are electrically connected to one another in parallel to form a bandstop filter. One of the first or second conductive terminals of the inductor is disposed generally adjacent to one of the first or second conductive terminals of the capacitor. The capacitor and the inductor may be aligned along a common axis, and the adjacent conductive terminals of the inductor and the capacitor may abut one another. An electrical insulator may also be disposed between the adjacent conductive terminals of the inductor and the capacitor.

The electrical potential between the adjacent conductive terminals of the inductor and the capacitor is preferably minimized, and is, ideally, zero.

The second conductive terminal of the inductor may be conductively coupled to the first conductive terminal of the capacitor, and the first conductive terminal of the inductor may be conductively coupled to the second conductive terminal of the capacitor.

A plurality of paired inductor and capacitor bandstop filters may be provided, wherein each bandstop filter is physically disposed in series relative to one another. In this case, each paired inductor and capacitor is electrically connected in series to another paired inductor and capacitor.

The capacitive component and the inductive component may comprise biocompatible and non-migratable materials and/or they may be disposed within a medically sealed container which forms the electromagnetic shield. The hermetically sealed container also forms an electromagnetic shield and may comprise a biocompatible housing in which the bandstop filter is disposed, and biocompatible first and second conductive contacts extending through and in non-conductive relation with the housing, which are conductively coupled in series to the bandstop filter. Typically, the hermetically sealed container is disposed in series in the implantable lead, wherein first and second contacts of the hermetically sealed container are connected to, respectively, proximal and distal portions of the lead.

A substrate may be provided onto which the inductor and capacitor are fixed in a pre-assembly prior to insertion into the biocompatible shield housing. First and second hermetic terminals hermetically sealed to the biocompatible housing after the pre-assembly is inserted therein may comprise at least a portion of the first and second conductive contacts, respectively. An electrically insulated conformal coating may be applied over at least a portion of the hermetically sealed container.

The overall Q of the bandstop filter is selected to balance impedance at the selected frequency versus frequency bandwidth characteristics. When the Q of the inductive component is relatively high, the Q of the capacitive component is relatively low such that the inductive component has a relatively low resistive loss and the capacitive component has a relatively high equivalent series resistance. When the Q of the inductive component is relatively low and the Q of the capacitive component is relatively high, the inductive component has a relatively high resistive loss and the capacitive component has a relatively low equivalent series resistance.

The active medical device (AMD) has a conductive equipotential surface, wherein the electromagnetic shield that substantially surrounds the inductive element or the passive network is conductively coupled to either the AMD equipotential surface or to surrounding body tissue. The AMD equipotential surface may comprise a conductive biocompatible housing for the AMD.

An energy diversion circuit may be provided which conductively couples the implantable lead to the electromagnetic shield. The energy diversion circuit may comprise a low pass filter such as a capacitor, an inductor, a Pi filter, a T filter, an LL filter or an "n" element filter. The energy diversion circuit may further comprise at least one series resonant L-C trap filter.

The energy diversion circuit may also comprise a high pass filter which prevents low frequency radiant field-induced energy in the implanted lead from passing through the diversion circuit to an energy dissipating surface or ground. The high pass filter may comprise a capacitor, a resistor in series with a capacitor, or an L-C trap filter.

An impeding circuit may be provided for raising the high frequency impedance of the implantable lead. The impedance circuit may comprise an inductor and/or a bandstop filter.

The electromagnetic shield may comprise the energy dissipating surface.

The inductive component may comprise a plurality of spaced apart inductive components disposed along the length of the implantable lead. In this case, not all of the inductive components need be shielded. Further, the electromagnetic shield may comprise a plurality of electromagnetic shields disposed along the length of the implantable lead. An adjacent pair of the plurality of electromagnetic shields are typically spread apart from one another but are also typically conductively coupled to one another.

The electromagnetic shield may comprise a conductive heat-shrink tubing, a conductive foil, wire, braid, mesh, circuit trace, or solid tubular material, or a conductive polymer, a conductive epoxy, carbon nano-fibers, nano-meshes, nano-coatings or nano-threads. The electromagnetic shield is further typically radially spaced from the passive component network.

The electromagnetic shield may comprise MP35N, iridium, carbon, platinum, titanium, palladium, chromium, Wolfram, tungsten, gold, copper, or alloys thereof. The inductive component may comprise a chip inductor, a solenoid inductor, a Wheeler spiral or a circuit trace inductor. Moreover, the implantable lead may comprise a plurality of implantable leads substantially surrounded by the electromagnetic shield. The AMD may comprise an implantable hearing device, a cochlear implant, a pisoelectric sound-bridge transducer, a neurostimulator, a brain stimulator, a cardiac pacemaker, a left ventricular assist device, an artificial heart, a drug pump, an implantable bone growth stimulator, a urinary incontinence device, a spinal cord stimulator, an anti-tremor stimulator, an implantable cardioverter defibrillator, or a congestive heart failure device.

Empirical data may be used to adjust the value of the inductance from the first inductive value to the second inductive value. Alternatively, an equivalent circuit model, such as PSPICE may be utilized to adjust the value of the inductance from the first inductive value to the second inductive value. Further, mathematical formulations based on a magnetostatic integral equation may be utilized to adjust the value of the inductance from the first inductive value to the second inductive value. Moreover, this ratio may be applied over the empirical inductance and divided by the inductance in the electromagnetic shield to adjust the value of the inductance from the first inductive value to the second inductive value.

The electromagnetic shield may comprise a housing for a passive fixation tip electrode or may be associated with a translational active fixation tip, wherein the housing for the active fixation tip comprises the electromagnetic shield. Alternatively, the electromagnetic shield may be disposed within a housing for the active fixation tip.

The network may include an active electronic circuit.

The shield may comprise a non-metallic material such as sapphire, ruby, alumina and/or ceramic materials which have a thin conductive coating deposited thereon by plating, chemical vapor deposition, sputtering, physical application, cladding or the like.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 59 is a perspective view of a reinforced polyimide tubing that includes the shielding for an inductive component in accordance with the present invention;

FIG. 60 is an enlarged sectional view taken generally along 60-60 from FIG. 59;

FIG. 61 is similar to FIG. 59, illustrating an alternative embodiment where an insulation tube is slipped over the lead and then a shield layer is slipped over the insulation tube;

FIG. 62 is similar to FIG. 61, except that the metal shield tube is replaced by wire wound strands;

FIG. 63 is similar to FIGS. 61 and 62, except that the metal shield tube or wire wound strands are replaced by wrapped foil;

DETAILED DESCRIPTION OF THE PREFERRED EMBODIMENTS

Figure 1:
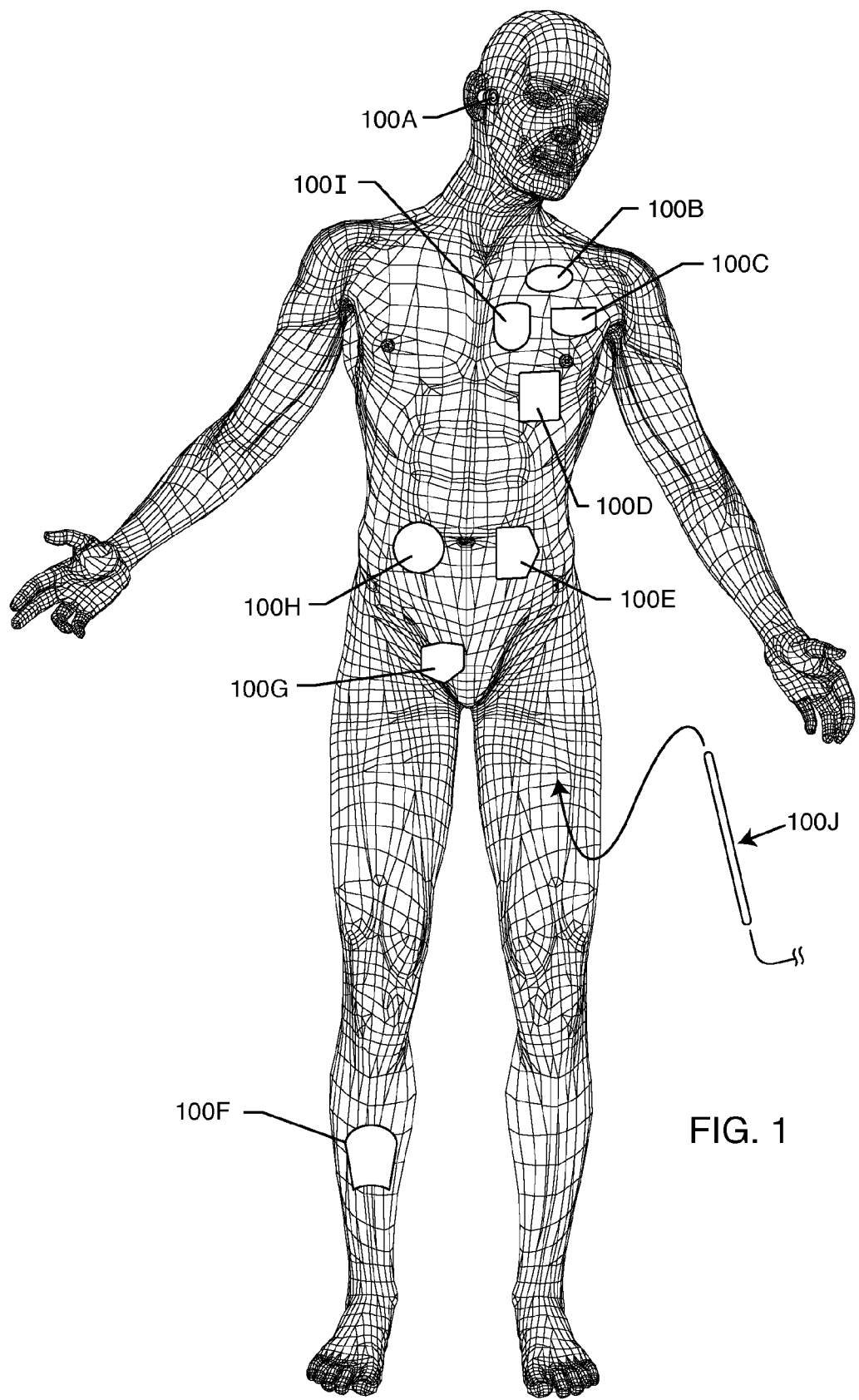
FIG. 1 is a wire-formed diagram of a generic human body showing a number of exemplary active medical devices (AMDs)

As shown in the drawings for purposes of illustration, the present invention relates to a system for RF shielding of a passive component or network disposed along the length of implanted leads of active medical devices (AMDs). In particular, the RF shielding is to shield a passive inductor or inductive component in the presence of high power electromagnetic field environments, such as the RF pulsed fields produced by a clinical MRI scanner. In a broad sense, the present invention comprises an active medical device system including an implanted lead having RF shielded inductors or passive network components including inductors. The implanted lead may be coaxial, rectangular, flat or other geometries. US 2009/0243756 incorporated herein by reference. Furthermore, the implanted lead may consist of a number of internal conductors, such as a bipolar lead for cardiac pacemaker channel or even an eight or sixteen conductor spinal cord stimulator implanted lead. This is also known as a multichannel lead system. The networks of the present invention can also include active components in combination with at least one inductor. These active networks can comprise a portion of a lead-based sensor, such as a hemodynamic sensor, a pulse oxygen sensor, an acceleration or rate sensor, and the like. In addition, the inductors of the present invention can be a part of an energy harvesting device or circuit which is implanted in the human body. US 2009/0243756 is incorporated by reference herein.

In general, the shield of the present invention surrounds all of the passive or active component elements disposed along the length of an implanted lead, including, but not limited to, inductors, inductor-capacitor (L-C) bandstop filters, L-C trap filters, or single or multi-element low pass filters. It is important that the shield surround at least the inductor component(s) associated with such electronic networks. As a practical matter, the shield would generally encompass all of the passive components. The shield could also surround all of the conductors in a particular implanted lead that is routed to a particular area of body tissue. For example, in a cardiac pacemaker application, there are often dual chamber bipolar conductors in the implanted lead, wherein one lead is typically routed to the right ventricle and the other to the right atrium. Each of these implanted leads, consisting of two conductors, would have its own passive component filtering elements which would be individually shielded. Typically, conforming to the shape of the leads, the shields of the present invention may be coaxial, flat, rectangular or any other geometry suitable for either tunneling or for transvenous insertion within the human body.

The shield of the present invention can also act as an energy dissipating surface. Diverting circuits, consisting of either capacitors, low-pass filter, L-C trap filters or high-pass filters, can be used to divert energy from an implanted lead to its surrounding shield. The shield, in a preferred embodiment, is in contact with body tissue whereby induced RF energy from the lead is diverted to the shield, which in turn acts as an energy dissipating surface (EDS). US 2010/0023000 A1 is incorporated herein by reference.

Implanted leads have both a characteristic impedance and also act as a transmission line. They tend to effectively couple energy from an external electromagnetic interference emitter as a function of their wavelength. This also varies with lead trajectory, design and other factors. However, when one is only concerned with particular frequency ranges, for example the RF pulse frequency of MRI, it is not necessary to shield the entire lead. In this regard, one could shield a significant portion of the lead so that the exposed (unshielded) portion of the lead was significantly less than a half or a quarter wavelength in body tissue. This makes the remaining unshielded lead portion a very inefficient antenna and therefore it would only pick up a very small amount of induced energy. Accordingly, in accordance with the present invention, one could shield passive network components or inductances disposed along the length of the shield and could also shield adjoining sections of the lead itself. By shielding a portion of the implanted lead or even segments of the implanted lead, one would break up its resonant lengths thereby making it a very ineffective antenna over a broad range of MRI pulsed frequencies.

The shields of the present invention can be a solid conductor, wound spiral conductors, meshes, tubing, nano-coatings or the like. In the preferred embodiment, the shield would present a fairly homogenous conductive surface such that it would effectively reflect and/or absorb incident electromagnetic fields. However, complete shielding is really not necessary. Accordingly, the shield could be loosely woven such that only a portion of the electromagnetic interference was intercepted.

The invention further resides in a combination of shields with one or more impeding circuits which could also be optimally combined with one or more diversion circuits. The impeding circuits typically would consist of either inductors or L-C parallel resonant-bandstop filters. The diversion circuits would typically consist of a capacitor, a multi-element low-pass filter, a high-pass filter, or an L-C trap filter. The operation of impeding circuits and diversion circuits is more thoroughly described in US 2010/0023000 A1 and US 2010/0160997 A1 which are incorporated by reference. In a particularly preferred embodiment, the shield of the present invention is used in combination with an impeding circuit known as a bandstop filter. The bandstop filter has a Q and 3-dB bandwidth such that, at resonance, it offers attenuation of at least 10 dB over a range of MRI RF pulsed frequencies at least 100 kHz wide.

In the case where bandstop filters are installed at or near the distal electrode of an implanted lead, the RF energy induced by the MRI pulse field is inhibited from flowing into body tissues and thereby being dissipated. However, even when distal electrode bandstop filters are used, that energy still resides in the lead system. In other words, by preventing this induced energy from flowing to sensitive tissues at distal electrode interfaces, a great deal has been accomplished; however, it is still important to carefully dissipate the remaining energy that is trapped in the lead system.

In order to provide optimal decoupling of RF energy from an implanted lead to the energy dissipating surface of a shield, one should consider Thevenin's maximum power transfer theorem. It is well known in electrical engineering that to transfer maximum power to a load, the load impedance must be equal to the source impedance. If the source impedance is completely resistive, for example, 50 ohms, then to transfer maximum power the load impedance would have to be 50 ohms. When the source impedance is reactive, then to transfer maximum power to another location the load impedance should have the opposite sign of reactance and the same impedance and resistance. In a typical implanted lead system, the implanted leads typically appear inductive. Accordingly, having a capacitive energy diversion circuit to couple energy from the lead conductors to the EDS shield surface, one has at least some cancellation of these imaginary impedance factors. In electrical engineering, the inductance of the lead would be denoted by $+j\omega L$. The impedance of the capacitor, on the other hand, is a $-j/\omega C$ term. Transferring maximal energy from a lead to an energy dissipating surface is more thoroughly described in U.S. Pat. No. 7,689,288 the contents of which are incorporated herein. It is important that the inductive elements of the diverter and/or impeding circuits be shielded in accordance with the present invention.

FIG. 1 is a wire formed diagram of a generic human body showing a number of exemplary implanted medical devices. 100A is a family of implantable hearing devices which can include the group of cochlear implants, piezoelectric sound bridge transducers and the like. 100B includes an entire variety of neurostimulators and brain stimulators. 100C shows a cardiac pacemaker. 100D includes the family of left ventricular assist devices (LVAD's) and artificial hearts. 100E includes an entire family of drug pumps which can be used for dispensing of insulin, chemotherapy drugs, pain medications and the like. 100F includes a variety of implantable bone growth stimulators for rapid healing of fractures. 100G includes urinary incontinence devices. 100H includes the family of pain relief spinal cord stimulators and anti-tremor stimulators. 100I includes a family of implantable cardioverter defibrillator (ICD) devices, congestive heart failure devices (CHF), and cardio resynchronization therapy devices, otherwise known as CRT devices. 110J illustrates a family of probes or catheters that can be transvenously inserted during catheter lab procedures. These are normally considered short-term implants in that they are inserted within the human body for at most a few hours.

The various types of active medical devices (AMDs) illustrated in FIG. 1 generally represent any type of AIMD that is considered a "long-term" implant. This is in direct contrast to things like probes or catheters or surgical devices that are "short-term" body insertions. For example, a probe or catheter is typically used in a cath-lab situation wherein it is temporarily inserted through a femoral (or other) artery where the entire procedure lasts minutes or at most a few hours. On the other hand, a long-term implant, such as a cardiac pacemaker, is generally designed to be implanted in the human body for many years. There are significant differences in the art between a short-term and a long-term implant. For example, for a long-term implant, one has to worry greatly about the long-term biocompatibility, toxicity and even the hermeticity of the implant. In contrast, a probe, catheter or temporary loop recorder need only operate or be reliable for a matter of minutes or even hours. In general, a short-term implant is often considered to be a disposable device. In addition, the FDA regulatory approval processes for long-term implants is significantly different and involves much more rigorous testing and product safety and reliability criteria. The FDA Center for Devices and Radiological Health (FDA-CDRH) is the responsible regulatory agency for long-term cardiac implants. As used herein, the term active medical device (AMD) is construed to include long-term implants and also short-term body insertions, such as probes or catheters. The term AMD is inclusive of active implantable medical devices (AIMDs) and also externally worn medical devices that are associated with an implanted lead.

Throughout, the term lead generally refers to implantable leads and their conductors that are external to the housing of the active medical device. These leads tend to have a proximal end, which is at or adjacent to the AMD, and a distal end, which typically includes one or more electrodes which are in contact with body tissue.

Figure 2:
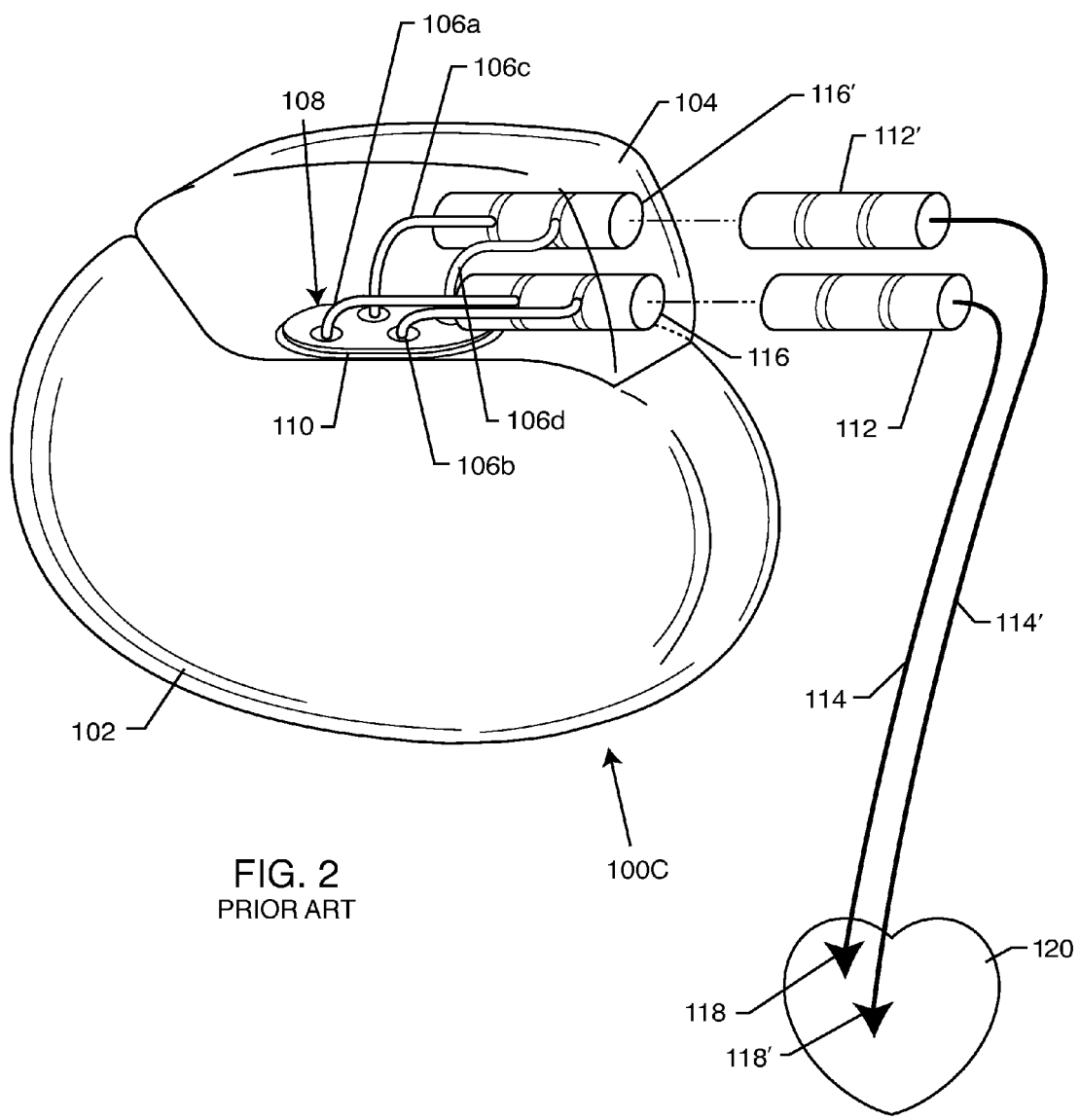
FIG. 2 illustrates an exemplary prior art cardiac pacemaker with the leads schematically shown extending to a patient's heart.

FIG. 2 is a drawing of a typical cardiac pacemaker 100C. showing a titanium case or housing 102 and an IS-1 header connector block 104. The titanium case or housing 102 is hermetically sealed, however there is a point where leadwires 106a-106d must ingress and egress a hermetic seal. This is accomplished by providing a hermetic terminal assembly 108 that generally consists of a ferrule 110 which is laser welded to the titanium housing 102 of the pacemaker 100C.

Four leadwires are shown consisting of leadwire pair 106a and 106b and leadwire pair 106c and 106d. This is typical of what is known as a dual chamber bipolar cardiac pacemaker. The IS-1 connectors 112 and 112' of leads 114 and 114' are designed to plug into receptacles 116 and 116' in the header block 104. The receptacles 116 and 116' are low voltage (pacemaker) connectors covered by an ANSI/AAMI ISO standard IS-1. Higher voltage devices, such as implantable cardioverter defibrillators (ICDs), are covered by ANSI/AAMI ISO standard DF-1. A new standard which will integrate both high voltage and low voltage connectors into a miniature in-line quadripolar connector is known as the IS-4 series. The implanted leads 114 and 114' are typically routed transvenously in a pacemaker application down into the right atrium 118 and the right ventricle 118' of the heart 120. New generation biventricular or CRT-P devices may introduce leads to the outside of the left ventricle, which devices have proven to be very effective in cardiac resynchronization and treating congestive heart failure (CHF).

Although the present invention will be described herein in the context and environment of a cardiac pacemaker 100C. and its associated leads 114 and 114', the present invention may also be advantageously utilized in many other types of AMDs as briefly outlined above, as well as in other commercial electronic, military, aerospace and other applications. In the following discussion, to the extent practicable, functionally equivalent components will retain the same or a similar reference number, irrespective of the particular embodiment being described.

Figure 3:
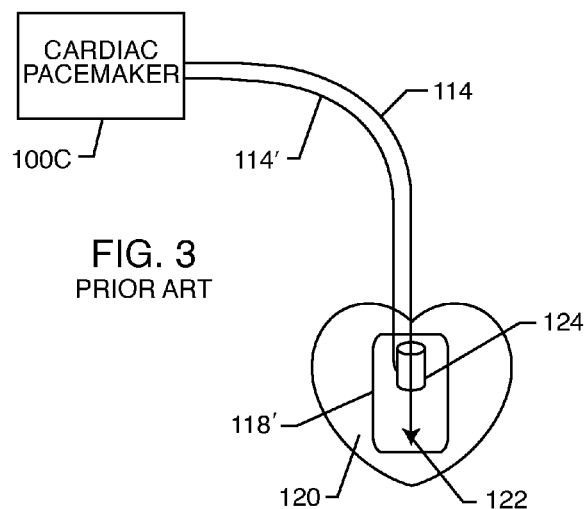
FIG. 3 is a schematic illustration of a prior art AMD with a bipolar lead.

FIG. 3 illustrates a prior art single chamber bipolar device 100C and lead system 114 and 114' with a distal tip electrode 122 and a ring electrode 124 typically as used with the cardiac pacemaker 100C. Should the patient be exposed to the fields of an MRI scanner or other powerful emitter used during a medical diagnostic procedure, currents that are directly induced in the lead system 114, 114' can cause heating by $I^2R$ losses in the lead system or by heating caused by RF current flowing from the tip and ring electrodes 122, 124 into body tissue. If these induced RF currents become excessive, the associated heating can cause damage or even destructive ablation to body tissue.

Figure 4:
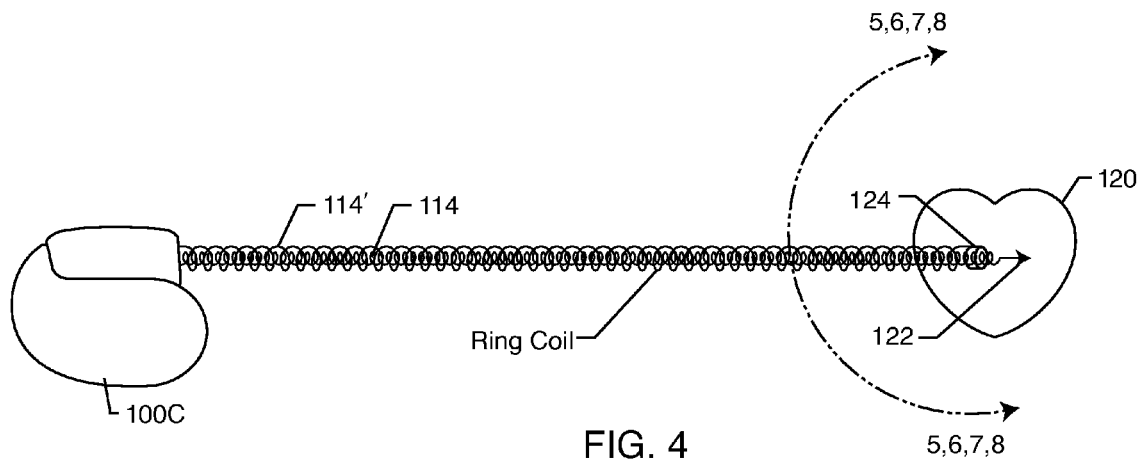
FIG. 4 is similar to FIG. 3, except that the bipolar lead wires are coaxially wound around one another.

FIG. 4 illustrates a single chamber bipolar cardiac pacemaker 100C, and leads 114 and 114' having distal tip 122 and distal ring 124 electrodes. This is a spiral wound (coaxial) system where the ring coil 114' is wrapped around the tip coil 114. There are other types of pacemaker leadwire systems in which these two leads lay parallel to one another (known as a bifilar lead system), which are not shown.

Figure 5:
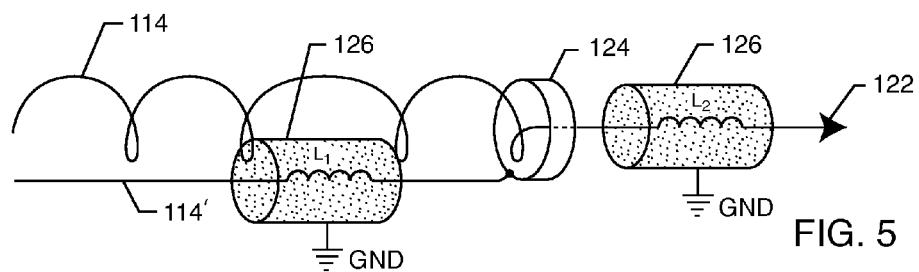
FIG. 5 is an enlarged schematic view of the area indicated by line 5-5 from FIG. 4, and illustrates an inductor disposed in series with each of a pacemaker tip and ring electrode circuits.

FIG. 5 is taken from section 5-5 of FIG. 4 and illustrates an inductor L disposed in series with each of a pacemaker tip and ring electrode circuits. The inductor L acts as a single element low pass filter and tends to attenuate the flow of current at high frequencies, such as MRI RF pulsed frequencies. The operation of inductors disposed in implantable lead wires is more thoroughly described in U.S. Pat. No. 5,217,010, the contents of which are incorporated herein. The shaded areas 126 in FIG. 5 illustrate that each of the inductors $L_1$ and $L_2$ has been shielded in accordance with the present invention. This protects the inductors $L_1$ and $L_2$ from picking up stray electromagnetic interference (EMI) from powerful RF fields of medical diagnostic equipment, such as an MRI scanner. For simplicity, the shields 126 are shown with a ground symbol (GND) indicating that they can be grounded in a number of ways. The important thing is that the shield 126 be able to reflect, absorb and dissipate RF energy that couples onto it. Electromagnetic shields both absorb and reflect incident high frequency energy. The energy that is reflected is not coupled onto the implanted lead. However, the energy that is absorbed is best converted to heat and dissipated into surrounding body tissues. Another method of grounding the shields is to connect a conductor back to the conductive housing 102 of the AMD itself. In general, the arrangement for a cardiac pacemaker shown in FIG. 5 is preferable in that the tip electrode inductor $L_2$ and the ring electrode inductor $L_1$ are individually shielded. It would be undesirable to have an overall electromagnetic shield to shield both the tip inductor $L_2$, the ring electrode 124 and the ring inductor $L_1$. This is because important cardiac pacing and biological signal sensing functions occur between the electrodes 122 and 124. Overall shielding of both tip and ring electrodes would impair said functions.

Figure 6:
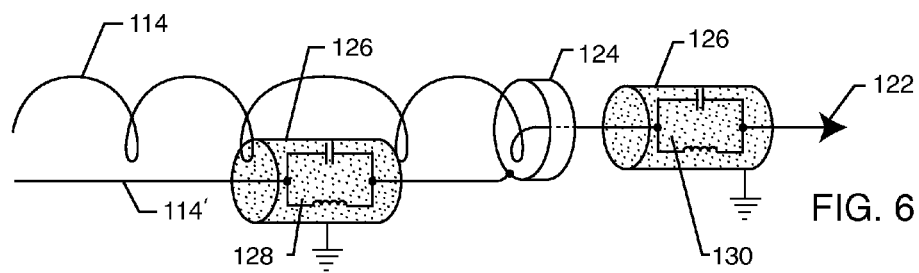
FIG. 6 is similar to FIG. 5 except that the inductor elements have been replaced by bandstop filters.

FIG. 6 is taken from section 6-6 of FIG. 4 and is very similar to FIG. 5. In this case, the inductor elements $L_1$ and $L_2$ have been replaced by L-C bandstop filters 128 and 130. In general, the shielded bandstop filters would be tuned to be resonant at a center frequency in a range of MRI RF pulsed frequencies. The operation of bandstop filters in implanted leads is more thoroughly described by U.S. Pat. No. 7,363,090 and US 2007/0112398, the contents of which are incorporated herein by reference.

Figure 7:
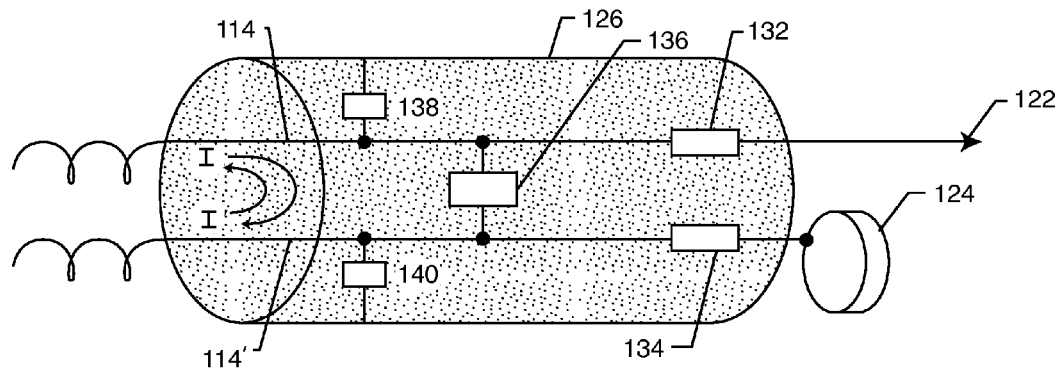
FIG. 7 is taken of the area indicated by line 7-7 from FIG. 4 and is similar to FIGS. 5 and 6, except that an overall shield encompasses various impeder and diverter elements.

FIG. 7 illustrates an AMD bipolar lead system similar to that described in FIGS. 5 and 6 except that an overall shield 126 encompasses various impeder elements 132 and 134 as well as diverter elements 136, 138 and 140. In this case, the impeder elements 132 and 134 could be inductors or bandstop filters as previously taught in FIGS. 5 and 6. The diverter elements could be capacitors or L-C trap filters as taught in U.S. Pat. No. 7,689,288, the contents of which are incorporated herein. In this case, both the tip electrode 122 and the ring electrode 124 are disposed outside the single shield 126 so they can still perform their vital cardiac pacing and biological sensing functions.

Figure 8:
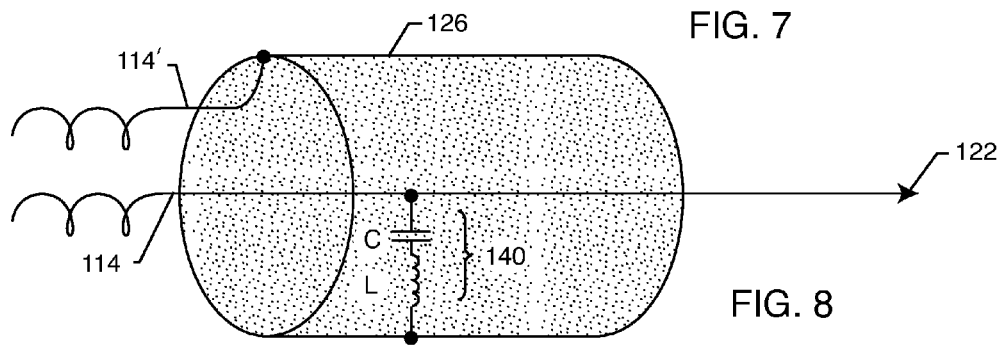
FIG. 8 is similar to FIG. 7, and illustrates a diverter element consisting of an inductor in series with a capacitor to form an L-C trap filter.

FIG. 8 is very similar to FIG. 7 and illustrates a diverter element 140 consisting of an inductor L in series with a capacitor C, forming what is known as an L-C trap filter. The operation of these trap filters is described in U.S. Pat. No. 7,689,288. The shield 126 protects the inductive component L of the L-C trap filter from picking up unwanted electromagnetic interference, for example, in an MRI RF field environment.

Figure 9:
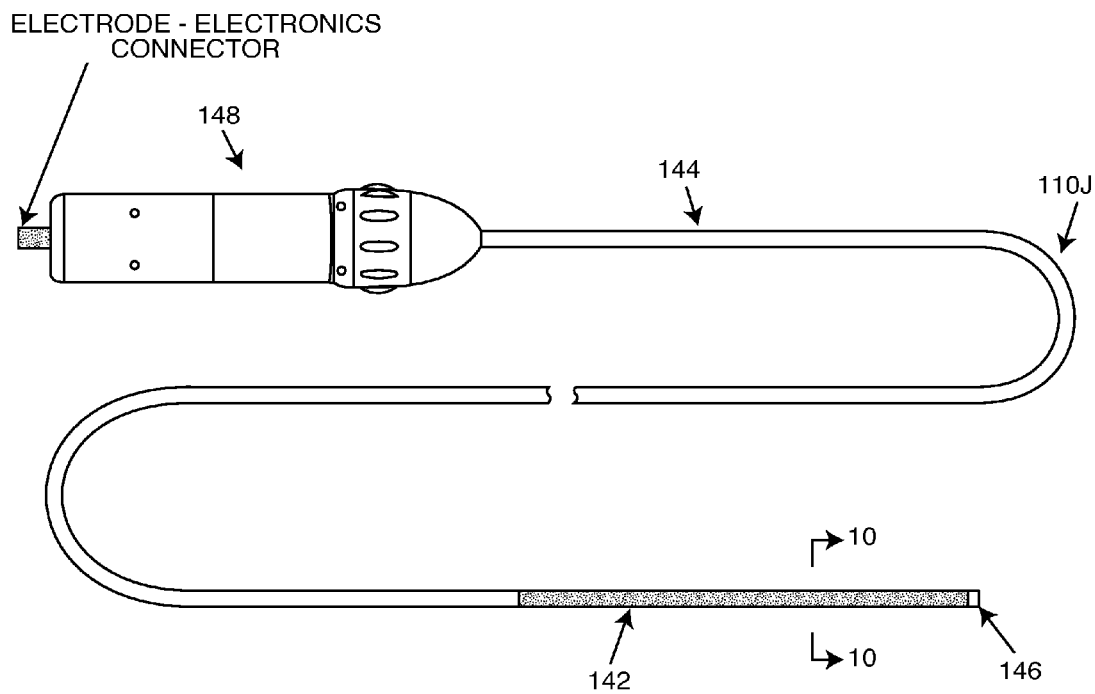
FIG. 9 illustrates a probe or catheter which has a shielded section embodying the present invention.
Figure 10:
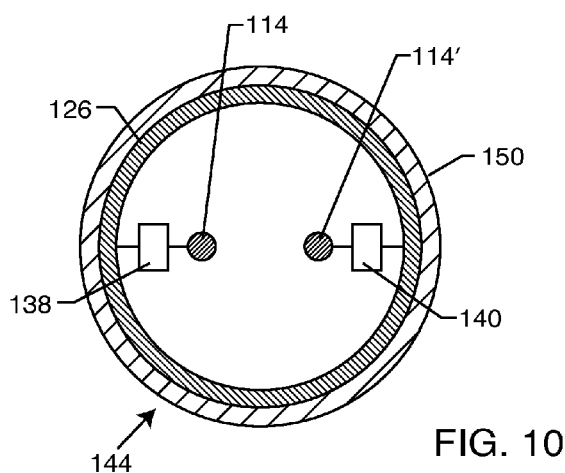
FIG. 10 is an enlarged sectional view taken along line 10-10 from FIG. 9.

FIG. 9 illustrates a probe or a catheter 100J which has a shielded section 142 which encompasses inductors or electronic networks of the present invention. The probe or catheter 100J consists of the flexible and steerable probe or catheter section 144 which may be bent as shown and generally terminates in one or more distal electrodes 146. These distal electrodes consist of mapping electrodes, ablation electrodes and the like. There is generally a catheter handle or body 148 which is used for steering the probe or catheter into the body transvenously. These handles can take the form of a pistol grip or many other shapes FIG. 10 is taken from section 10-10 of FIG. 9 and shows two leads inside the flexible portion 144 of the probe or catheter. Shown are diverter elements 138 and 140 which are connected between each of the leads 114 and 114' to the electromagnetic shield 126 of the present invention. In a preferred embodiment, the diverter elements would be L-C trap filters which would be used to divert energy picked up on the leads 114 and 114' to the shield surface 126. An optional insulation sleeve 150 is shown, which is generally undesirable. In other words, it is preferable that the conductive shield 126 be in contact with body tissue so that it dissipates unwanted MRI RF energy over a large surface area. The electromagnetic shield 126 of the present invention protects the inductor element of the L-C trap filters 138 and 140 from picking up unwanted high frequency RF energy.

In the description of the various embodiments shown in the accompanying drawings, the functionally equivalent components shall have the same reference number.

Figure 11:
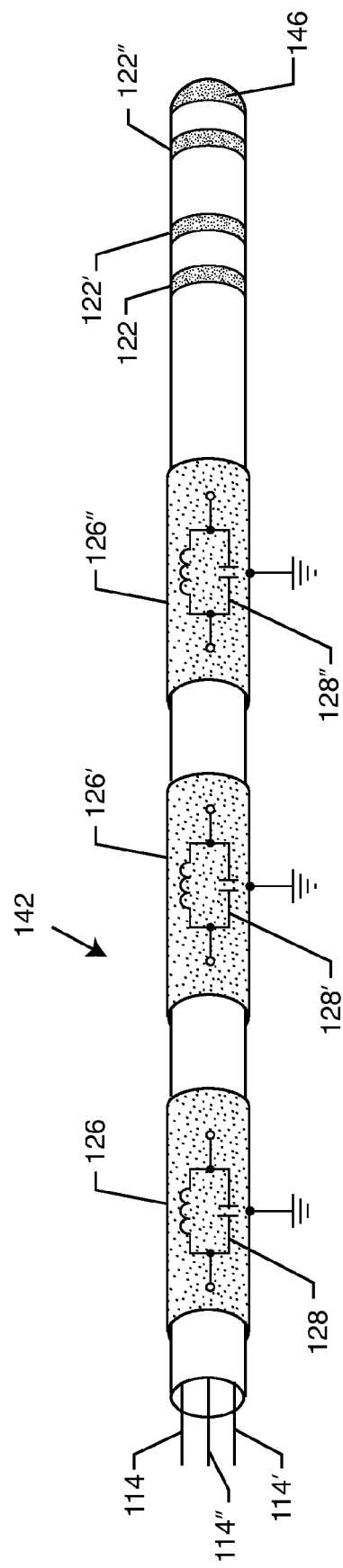
FIG. 11 is an enlarged view of the distal tip section of the probe or catheter of FIG. 9.

FIG. 11 is an alternative to the shielded portion 142 of the probe or catheter 100J illustrated in FIGS. 9 and 10. In this case, there are three internal conductors 114, 114' and 114" disposed within the flexible catheter portion 142. There are also three segmented shields 126, 126' and 126" for a respective bandstop filter 128, 128' and 128". Each of the bandstop filters 128, 128' and 128" are connected in series with a respective one of the catheter conductors. In this case, the shields 126, 126' and 126" could be continuous or segmented as shown. There is an advantage to segmented shields as this promotes the flexibility of an implanted probe, catheter or AMD lead. In addition, segmented shield sections break up transmission line type resonances and change the wavelength of the implanted lead to make it a much less efficient RF antenna. One can see that there are sensing electrodes 122, 122' and 122" for mapping biological signals, and a tip electrode 146 for ablating or creating scar tissue to eliminate unwanted arrhythmias such as atrial fibrillation.

Figure 12:
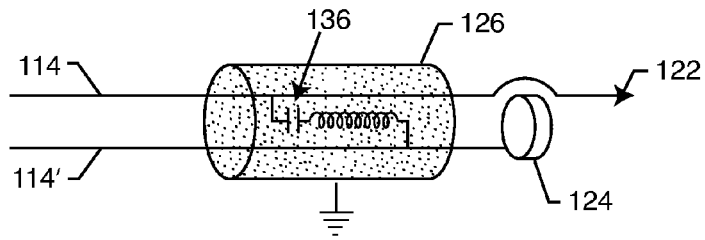
FIG. 12 is similar to FIG. 5 except that it has a single shield for a differential mode L-C trap filter.

FIG. 12 is very similar to FIG. 5 except that it has a single shield 126 which shields an L-C trap filter 136 which is connected between lead 114 and lead 114'. In the art, this is known as a differential mode L-C trap filter.

Figure 13:
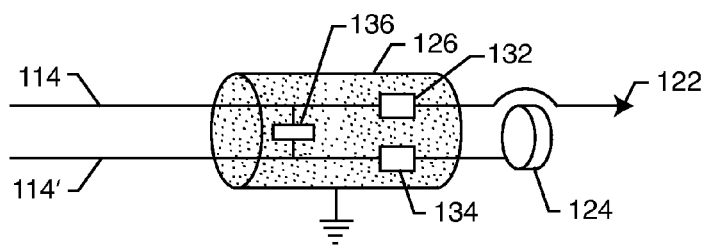
FIG. 13 is similar to FIG. 12, except that the L-C trap filter has been replaced by a general diverter element.

FIG. 13 is similar to FIG. 12 except that the L-C trap filter 136 has been replaced by a general diverter element. In this case, the diverter element 136 can be an L-C trap filter, a number of multi-element low pass filters or single element capacitive filters. These are shown combined with impeder elements 132 and 134. The impeder element would typically include an inductive component.

Figure 14:
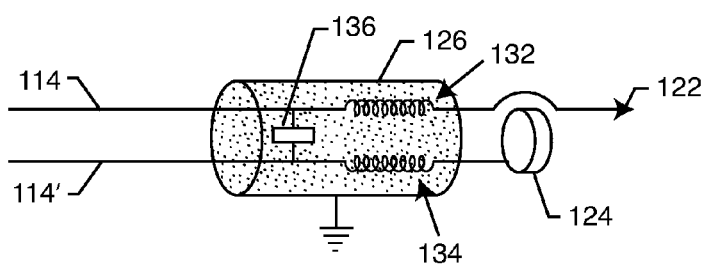
FIG. 14 is similar to FIG. 13, wherein the impeder elements are inductors.

FIG. 14 illustrates the embodiment of FIG. 13 wherein the impeder elements 132 and 134 are inductors.

Figure 15:
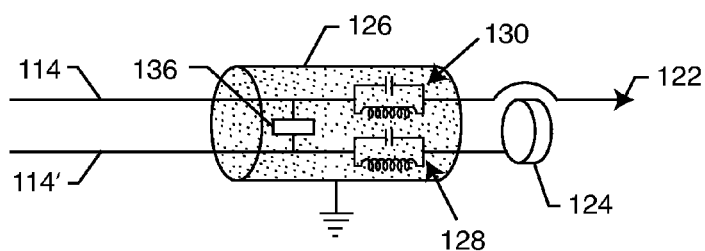
FIG. 15 is similar to FIGS. 13 and 14, wherein the impeder elements are bandstop filters.

FIG. 15 is very similar to FIG. 13 wherein the impeder elements are bandstop filters 128 and 130. These bandstop filters would normally be tuned to be resonant at an MRI RF pulsed frequency or range of frequencies.

Figure 16:
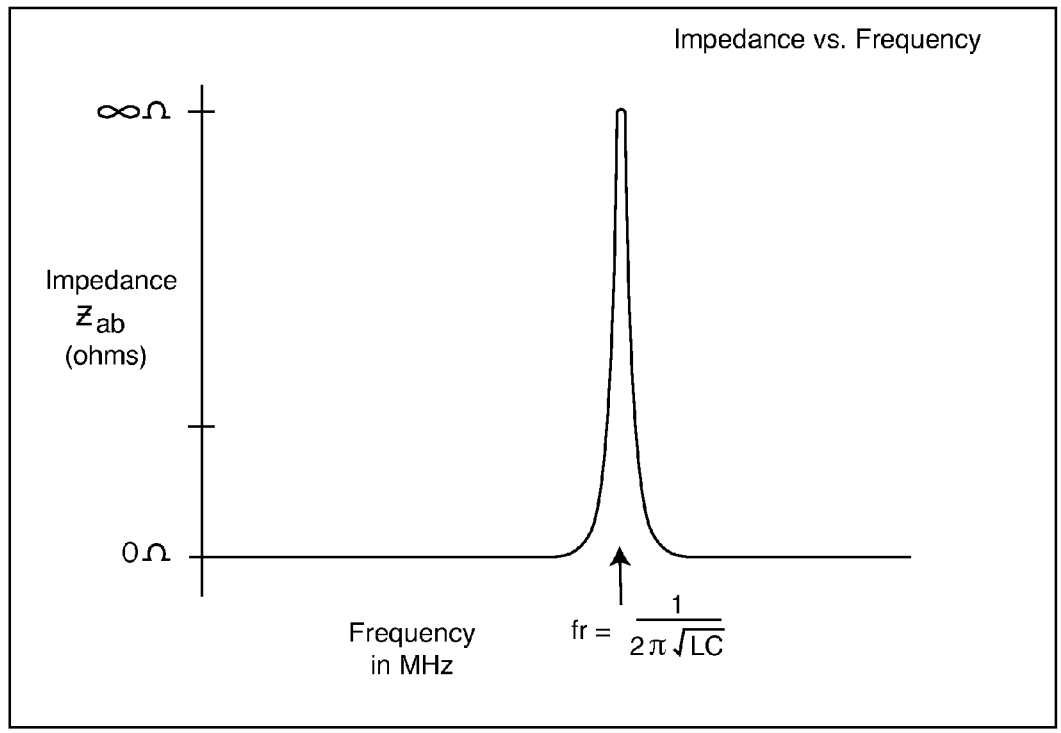
FIG. 16 is a graph showing impedance versus frequency for the ideal bandstop filter circuit of FIGS. 6 and 15.

FIG. 16 is a graph showing impedance versus frequency for the ideal parallel bandstop filter circuit 130 of FIG. 6 or 15. As one can see, using ideal (zero resistance) circuit components, the impedance measured between the lead 114 and the tip electrode 122 is zero until one approaches the resonant frequency $f_r$. At the frequency of resonance, these ideal components (the parallel inductor L and capacitor C) resonate together to approach an infinite impedance. In general, the frequency of resonance $f_r$ is given by the equation shown in FIG. 16 and is selected to be the center frequency of an MRI RF pulsed frequency. For example, for a 1.5 Tesla hydrogen scanner, the RF pulsed frequency as determined by the Lamour equation is 42.56 times the magnetic field strength in Tesla. This is approximately 63.84 MHz. Accordingly, the resonant frequency of the bandstop filter 130 would be selected to be centered approximately around 63.84 MHz.

It should be noted that not all 1.5 Tesla MRI scanners have exactly the same static magnetic field strength. This results in variation of the RF pulsed frequency by over ½ MHz. It is desirable that the bandstop filters 128 and 130 provide substantial attenuation or 3 dB bandwidth over this entire range. Similar variations occur for other commonly labeled MRI scanners, such as 3 Tesla scanners.

Figure 17:
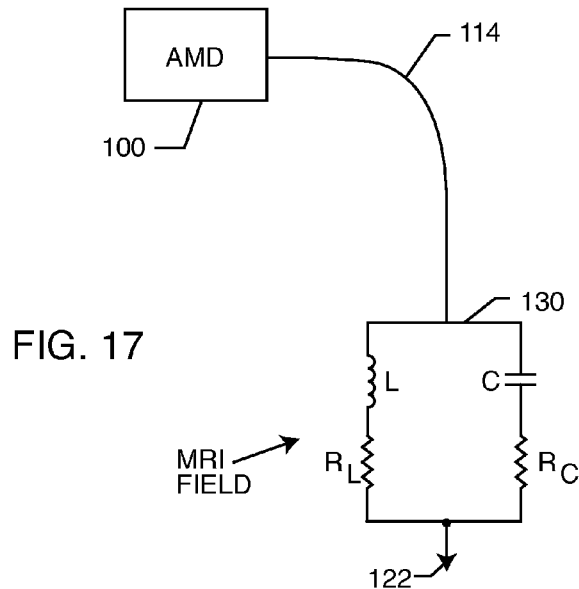
FIG. 17 is a schematic illustration similar to FIG. 3, showing a generic unipolar AMD and lead with a bandstop filter added at or near a distal electrode.

FIG. 17 is a drawing of a generic unipolar AMD 100 and lead 114, with a bandstop filter 130 added at or near the distal electrode 122. The inductor L has a resistance element $R_L$ in series with it. The capacitor C also has a resistance $R_C$ in series with it. The resistances $R_L$ and $R_C$ can be separate discrete resistors or they are losses of the inductor and capacitor elements themselves. In general, the resistance $R_L$ will be the resistance of the circuit traces or wires used to form the inductor L. The capacitor C has ohmic losses $R_C$ due to the resistance of its internal electrode plates, connection to its electrode plates, and dielectric losses. In the capacitor industry this is known as the capacitor's equivalent series resistance or ESR. The bandstop filter circuit 130 illustrated in FIG. 17 is a "real" bandstop filter in that the resistive losses are included. This makes it distinct from the ideal bandstop filter circuit shown in FIGS. 6 and 15. The presence of the bandstop filter 130 will present a very high impedance over a specific range of MRI RF pulsed frequencies to prevent currents from circulating through the distal electrode 122 into body tissue at this specific frequency range.

Figure 18:
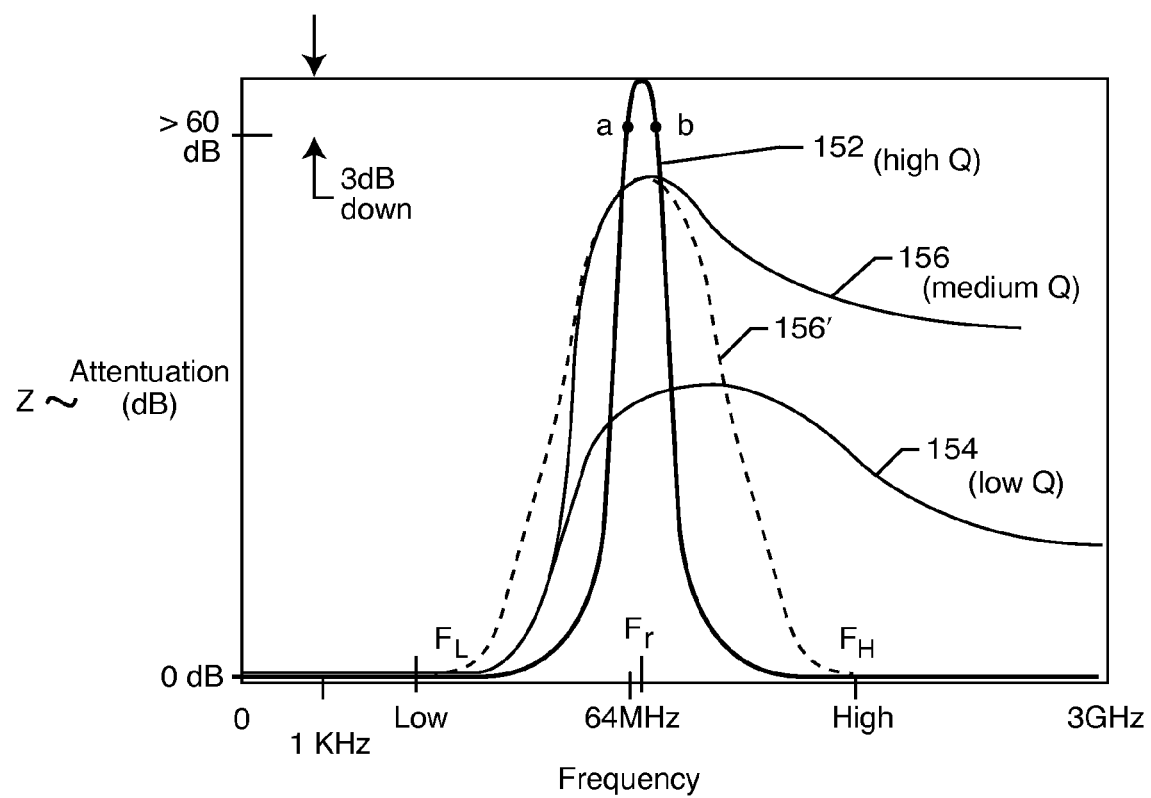
FIG. 18 illustrates a family of curves which show the attenuation in dB versus frequency for bandstop filters.

FIG. 18 is a family of curves 152, 154, 156 and 156' which show the attenuation in dB versus frequency for the bandstop filters 128 and 130. Curve 152 represents the use of very high Q inductor and capacitor components. If the capacitor and the inductor were ideal, meaning that they would both have zero resistance, then there would be no 3 db bandwidth at all between points "a" and "b". However, since in the real world both the inductor and the capacitor do have losses, a 3 db bandwidth separation between points "a" and "b" is achieved. It is very important that there be suitable bandwidth for two reasons: one, the MRI machine has gradient fields which change the RF frequency. This is how the MRI machine selects a slice to image, for example, through the knee. It does this by modifying (grading) the 1.5 Tesla or main static field by using a gradient field. This causes the Lamour frequency to change. Accordingly, one can see that some bandwidth is required centered around the specified pulsed resonant frequency of the MRI equipment so that all of these frequencies are properly attenuated in an implanted lead. If one were to deliberately use an inductor with a very high DC resistance and a capacitor with very high ESR, this would result in very low Q components and the resulting attenuation curve 154. The low Q attenuation curve 154 attenuates over a very broad range of frequencies; however, the amount of attenuation in dB has been sacrificed. In general, in practice, it is easier to purchase monolithic ceramic capacitors with relatively high Q values. Accordingly, the Q of the inductor L can be controlled by increasing $R_L$. Accordingly, it is a feature of the present invention that the resistance of the inductor be controlled to also control the overall Q and resulting 3 dB bandwidth of the parallel resonant bandstop filter 128, 130.

Attenuation curves 156 or 156' shown in FIG. 18 are generally preferred. One can do this by controlling the relative Q of the inductor and the capacitor components of the bandstop filter 128, 130. In one embodiment (156'), the Q of the inductor would be relatively low and the Q of the capacitor would be relatively high. This means that the inductor would have a relatively high internal resistance and the capacitor would have a relatively low equivalent series resistance. This is achieved by using multiple turns of relatively small wire to create a high DC resistance in the inductor, and by using multiple and robust electrode plates to keep the equivalent series resistance (ESR) of the capacitor relatively low. The overall Q of the bandstop filter is thus selected to balance impedance at the selected frequency versus frequency bandwidth characteristics. The values of the inductor and the capacitor selected are such that the bandstop filter 128, 130 is resonant at a selected frequency, and preferably selected to attenuate current flow through the lead or electrode along a range of selected frequencies. Such a frequency or range of frequency may include an MRI RF pulsed frequency. Typically, the Q of the inductor is relatively low or moderate, and the Q of the capacitor is relatively high or moderate to select the overall Q of the bandstop filter. That is, the inductor has a relatively high resistive loss $R_L$, and the capacitor has a relatively low equivalent series resistance $R_C$.

For medical implant applications it is very important that the implanted leads and their associated electrodes at the distal tips be very small. It is particularly important that the cross-sections or diameters of the bandstop filters be very small for easy endocardial insertion into the venous system of the human body. The present invention meets these criteria by using a novel combination of components that are mechanically mounted in series, but whose lumped elements are electrically in parallel. The components generally consist of commercial off-the-shelf miniature chip capacitor and inductor components. These are generally manufactured in high volume throughout the world. Accordingly, they are very inexpensive, but more importantly, they are very small in size. By way of example, twenty years ago a small sized monolithic chip capacitor (MLCC) would be 0603, meaning that it would be 0.060 inch long by 0.030 inch in width. In comparison, current inductor and capacitor chip components can be purchased as small as 0201 or 01005. This means that they are so small that they literally can fit through a pepper shaker. Human hands generally cannot assemble components this small. Accordingly, micro-robotic manufacturing is the preferred method of manufacturing the novel components assemblies of the present invention, wherein the components typically are delivered on tape and reel and fed into the robots which pick and place the components and then go through a series of steps including additional component placement, wave soldering, cleaning, automatic optical inspection and automated electrical testing. All of this is done in a linear robotic manufacturing operation that is completely or nearly free of human hands. In cardiac rhythm applications (pacemakers and ICDs), a desirable lead size is 6 French (0.079 inches in diameter). For deep brain stimulator applications, an even smaller size is desirable, such as 3 French, which is 1 millimeter in diameter or 0.039 inches. US 2007/0112398 A1 discloses a number of methods of manufacturing novel bandstop filters for placement in the lead systems of active implantable medical devices. The present invention extends these concepts further.

In mammalian implant applications, the shielded inductors, diverters, impeders, and bandstop filters of the present invention should be small and placed in series with the implanted lead or electrode of the medical device. In general, the diameter is much more important than the volume or length of the passive network package to be placed in series with an implanted lead 114, 114'. This is because leads are typically introduced into the human body either by tunneling or transvenous insertion. In such applications, it is necessary that the shielded lead component assembly be EMI shielded, biocompatible and highly reliable. Although commercial off-the-shelf capacitor and inductor components are very small in size, arranging them such that they are electrically coupled in parallel can increase the size of the bandstop filter where complications can arise in the placement and use of the implanted lead or electrode.

Commercial off-the-shelf capacitor and inductor components are typically not entirely comprised of biocompatible materials. However, in accordance with the present invention, the shielded inductor L and capacitor C elements can be constructed to be completely biocompatible. In this case it would be not necessary to place them in a biocompatible hermetic container. Just an open ended EMI shield would suffice. This would have great advantages in further reducing both size and cost. In this regard, US 2009/0116167, U.S. Pat. No. 7,535,693, and US 2009/0259265, are incorporated by reference.

Figure 19:
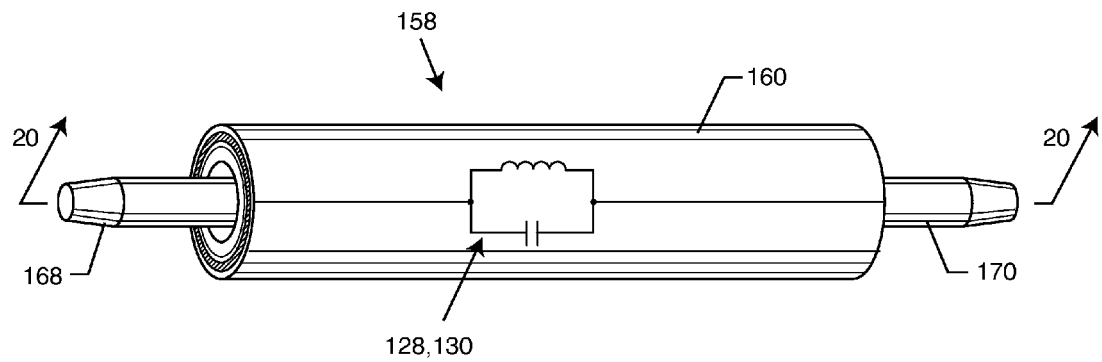
FIG. 19 illustrates a hermetically sealed container for a bandstop filter embodying the present invention.

With reference to FIG. 19, it is a feature of the present invention that custom or "off-the-shelf" non-biocompatible miniature inductor L and capacitor C components are mechanically installed in shielded (conductive) hermetic packages or containers 158 in series, but have electrical circuit traces that couple the lumped inductor and capacitor elements electronically in parallel, thereby forming bandstop filters 128, 130 as described above. FIG. 19 illustrates a hermetically sealed shielded container 158 having the inductor (L) and capacitor (C) components installed therein in series with one another, but whose lumped L and C elements are coupled electronically in parallel, so as to form one or more bandstop filters 128, 130. The shielded housing 160 for the hermetically sealed container 158 is very small in diameter or cross-section and can be disposed between portions of an implantable lead 114, within an electrode assembly, etc.

Figure 20:
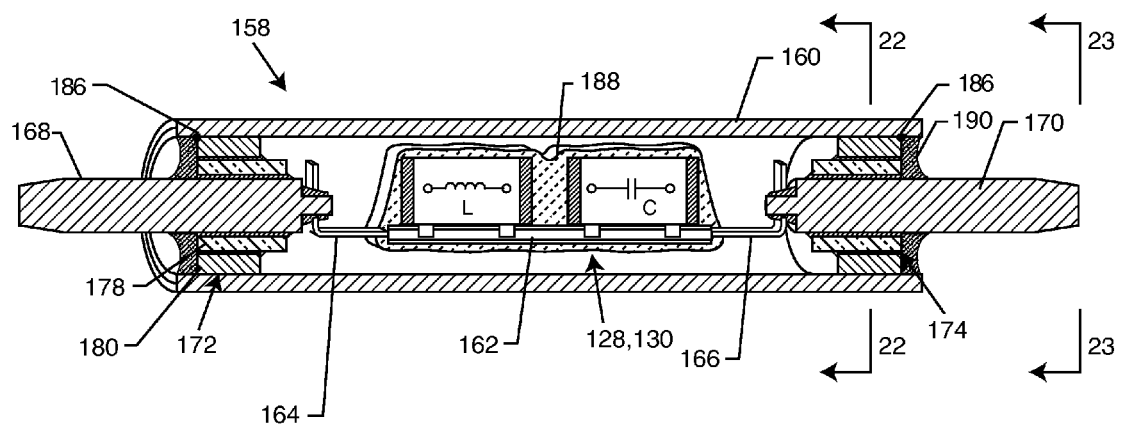
FIG. 20 is an enlarged sectional view taken generally along line 20-20 from FIG. 19.

FIG. 20 is a cross-sectional view taken generally along line 20-20 of FIG. 19 and shows the various component parts of the shielded hermetically sealed container 158. The shielded housing 160 can be comprised of a biocompatible metal or alloy, such as titanium, platinum, platinum-iridium, gold, palladium, tantalum, carbon, niobium, etc., or alloys thereof. The shielded housing 160 can also be a non-metallic material, such as sapphire, ruby, lumina, ceramic, glass, etc, having a thin layer of conductive metal deposited on either its inside or outside surface. For example, if the non-metallic shield was cylindrical, a metal coating could be applied to its outside diameter. In this case, the metal coating should be biocompatible and could be applied by electroplating, sputtering, chemical vapor deposition, cladding, or the like. The inductor L and the capacitor C are disposed on a substrate 162 and physically arranged in series, or end-to-end with one another, yet conductively or electronically coupled to one another in parallel. Circuit traces 164 and 166 are conductively coupled to the inductor L and capacitor C of the bandstop filter 128, 130 and extend to conductive terminals 168 and 170 of hermetic seal assemblies 172 and 174. The conductive terminals 168 and 170 are designed to be conductively coupled to portions of the implantable lead 114, 114' or electrode assembly.

Figure 21:
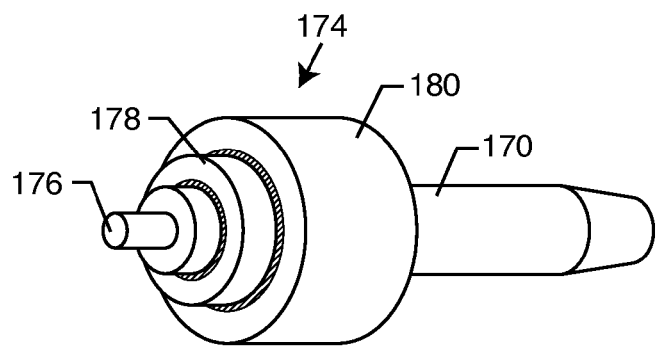
FIG. 21 is an enlarged perspective view of the hermetic seal assembly from FIG. 20.

FIG. 21 is an enlarged perspective view of the hermetic seal assembly 174 from FIG. 20, having the terminal 170 extending therethrough to a crimp, solder joint or laser weld tip 176. The electrical connection to the tip 176 could also be formed by thermal-setting conductive adhesives. The terminal 170 is attached to an insulator 178, which is in turn attached to an outer ferrule 180.

Figure 22:
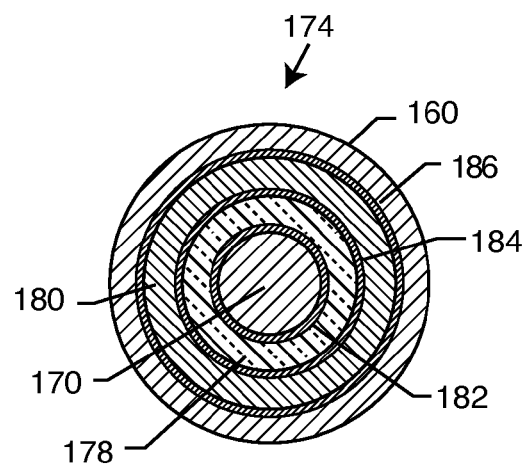
FIG. 22 is an enlarged cross-sectional view taken generally along the line 22-22 from FIG. 20.

FIG. 22 is a cross-section drawing taken along line 22-22 from FIG. 20. The terminal 170 is preferably of a common platinum-iridium alloy, such as 9010 or 8020. However, any biocompatible and suitable material could be used in place of platinum-iridium. Gold braze 182 forms a hermetic seal between terminal 170 and insulator 178. The insulator 178 may be a polished sapphire, ruby, polycrystalline alumina, or even glass or a general ceramic material. Sputtering would first be deposited on the surfaces so that the gold braze 182 will readily adhere and wet. Gold braze 184 forms a hermetic seal between insulator 178 and the ferrule 180. Gold brazes 182 and 184 are generally pure gold brazes for biocompatibility and long term reliability. The surface preparation process for the ceramic insulator 178 can be as follows: C-Axis single crystal, polycrystalline alumina (A12O3), Zirconia Stabilized Alumina and/or Yttria Tetragonal Zirconia Polycrystalline YTZP is etched using RF plasma before PVD sputtering using a biologically compatible metallic system. Plasma cleaning removes organic surface contamination and hydroxyl/oxides resulting in a higher energy surface. This activated surface readily forms strong covalent bonds with metallization atoms promoting robust, hermetic adhesion. Through industry standard process refinements, the resulting low stress, dense coating does not spall off or blister and improves the function and reliability of the final brazed joint. The outer ferrule 180 is also, preferably, of platinum-iridium since it's very easy to laser weld. It is also radio-opaque.

In the preferred embodiment, the insulator 178 would be a polished sapphire. It would then go through a plasma-etch process, such as a 500 watt plasma-etch, to increase its surface roughness. Titanium-molybdenum or niobium metallization would be a preferred sputter material for adhesion and wetting of the associated gold braze pre-forms.

Figure 23:
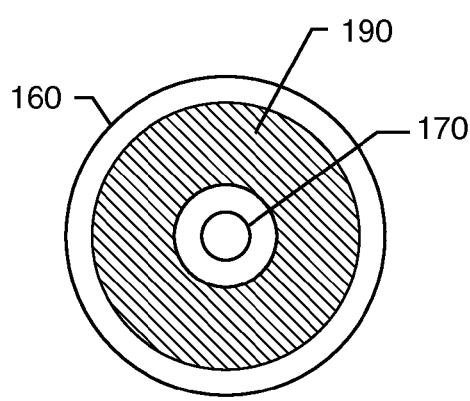
FIG. 23 is an end view of the hermetic seal assembly of FIG. 21, taken from line 23-23 in FIG. 20.

In FIGS. 20 and 21, one can see that the interior tip 176 of the terminals 168 and 170 has been extruded to be fitted into an aperture, socket, etc. of the conductive substrate or circuit traces 164 and 166. Alternatively, the interior tip 176 may have an aperture therethrough so that a crimped connection can be formed between it and the conductive substrate or circuit traces 164 and 166, and subsequently laser welded. The method of attachment to the interior tip 176 will vary in accordance with the type of attachment desired to the internal circuitry of the bandstop filter 128, 130. In any event, the conductive terminals 168 and 170 are conductively coupled to the bandstop filter 128, 130 as the associated hermetic seal assemblies 172 and 174 are slid into place and hermetically sealed by laser welding 186 to the housing 160 of the container 158. FIG. 23 is an end view taken along line 23-23 in FIG. 20.

Again, FIG. 20 shows the bandstop filter 128 and 130 comprised of the inductor L and capacitor C, and the flexible circuit substrates 164 and 166 extending therefrom, attached to the terminals 168 and 170 so as to place the terminals 168 and 170 in electrical series with one another. However, the inductor L and the capacitor C, although placed end-to-end and physically in series with one another, are conductively coupled electrically with one another in parallel. An insulating material 188, such as a thermal-setting non-conductive polymer, at least partially fills the remainder of the EMI shield housing 160 to provide protection and mechanical robustness to the overall container assembly 158. This structure lends itself to a novel "ship-in-the-bottle" method of manufacturing. That is, all of the elements contained within the shield housing 160 are pre-assembled outside the housing. In particular, the terminal 168, the substrate 162 containing the inductor L and capacitor C, and the opposite terminal 170 and the associated hermetic seals 172 and 174, are all pre-assembled outside of the overall EMI shield housing 160. This facilitates proper electrical connections and electrical testing of the pre-assembly. In addition, this entire subassembly can go through high reliability screening. Typically, this would consist of thermal cycling or thermal shock followed by a burn-in, which means applying a relatively high voltage at elevated temperature to the circuit components and then comprehensive electrical test afterwards. Once all of this has been done, this entire pre-assembly is slipped inside the overall cylindrical EMI shield housing 160 and then a final laser weld 186 is formed.

FIG. 20 also shows an optional conformal coating 190 which is provided over the two gold brazes 182 and 184. This conformal coating 190 could also be applied to the entire outer surface of the housing 160 and a portion of terminals 168 and 170, as well as optionally over the electrical attachments to the lead system. This conformal coating 190 is important to provide electrical isolation between the two terminals 168 and 170. When directly exposed to body fluids (which contain electrolytes), gold can migrate in the presence of a voltage bias. It has been shown that pacemaker pacing pulses in saline solution can actually cause a gold electromigration or electroplating action. The concern is that the gold braze materials 182 and/or 184, under voltage or pulse bias, may over time migrate or deposit (electro-plate) onto another surface such as the terminal 170 or the housing 160, which could negatively affect the long-term hermeticity and reliability of the hermetic seal assembly 174. Accordingly, the conformal coating or backfill 190 is placed as shown to cover both of the gold brazes 182 and 184. The conformal coating 190 may comprise thermal-setting non-conductive adhesives, silicones, parylene (which is vapor deposited), and the like, including epoxies, polyimides, polyethylene oxide, polyurethane, silicone, polyesters, polycarbonate, polyethylene, polyvinyl chloride, polypropylene, methylacrylate, paraxylylene, and polypyrrhol. In particular, Epo-tek H81 is considered a preferred epoxy which has already been tested for long-term biocompatibility. The importance of providing electrical isolation across components, such as bandstop filters, is more thoroughly described in U.S. patent application Ser. No. 12/873,862 which is incorporated herein by reference.

A complete conformal coating 190 over the entire shield housing 160 may be desirable to provide electrical isolation between the conductive terminal pins 168 and 170. This provides critical performance capability in the event of complete saturation of the housing 160 in saline or biological fluid. Additional performance benefits for a conformal coating 190 include lubricity, radiopacity, and wear resistance.

Figure 24:
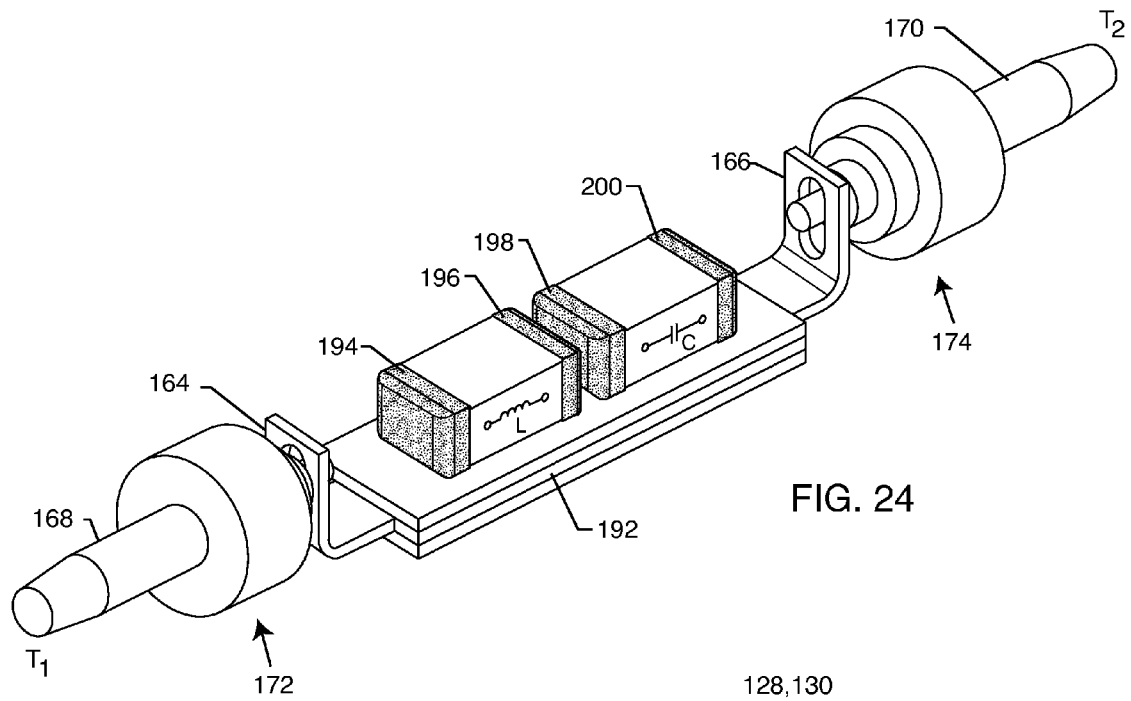
FIG. 24 is a perspective view illustrating a multi-layer flex cable onto which the inductor and capacitor of FIG. 20 are mounted.
Figure 25:
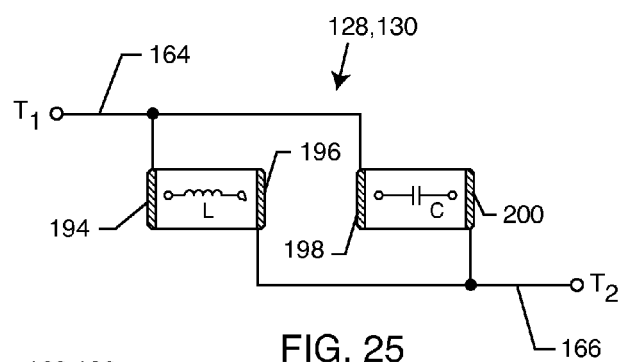
FIG. 25 is a schematic illustration showing that the inductor and capacitor are physically disposed in series relative to one another and yet electrically connected in parallel.
Figure 26:
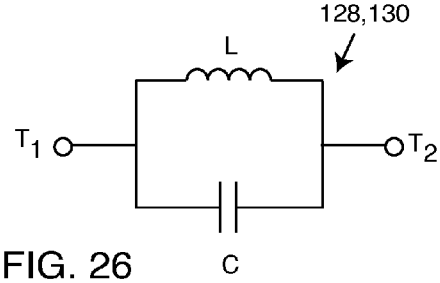
FIG. 26 is an electrical schematic diagram of the bandstop filter of FIGS. 24 and 25.

FIG. 24 illustrates a multi-layer substrate or flex cable 192 onto which the inductor L and capacitor C are mounted. The inductor L is a chip inductor having first and second conductive termination surfaces 194 and 196 which are spaced from one another in non-conductive relation. The capacitor C also has first and second conductive termination surfaces 198 and 200 which are spaced apart from one another in non-conductive relation. The chip inductor L can be any number of chip inductor types, however the present invention is also not limited to chip inductors only. The inductor L could also be a solenoid inductor, a toroidal inductor, or any type of inductor that is known in the prior art. Moreover, the chip capacitor C can be any number of chip capacitor types, but the present invention is not limited to chip capacitors only. The capacitor C may be of many different types of capacitor technologies, including film capacitors, tantalum capacitors, monolithic ceramic capacitors, electrolytic capacitors, feedthrough-type capacitors, or even tubular capacitors. FIGS. 24 and 25 show that the inductor L and the capacitor C are physically disposed in series relative to one another, such that they are generally aligned with one another along a common longitudinal axis and placed end-to-end. However, as shown in FIGS. 25 and 26, the inductor L and the capacitor C are conductively or electrically coupled to one another in parallel. FIG. 26 is an electrical schematic diagram of the bandstop filter 128, 130 of FIGS. 24 and 25. For a more complete description of how to dispose implantable lead components physically in series but electrically in parallel, reference is made to US 2010/0100164 A1, the contents of which are incorporated herein.

Figure 27:
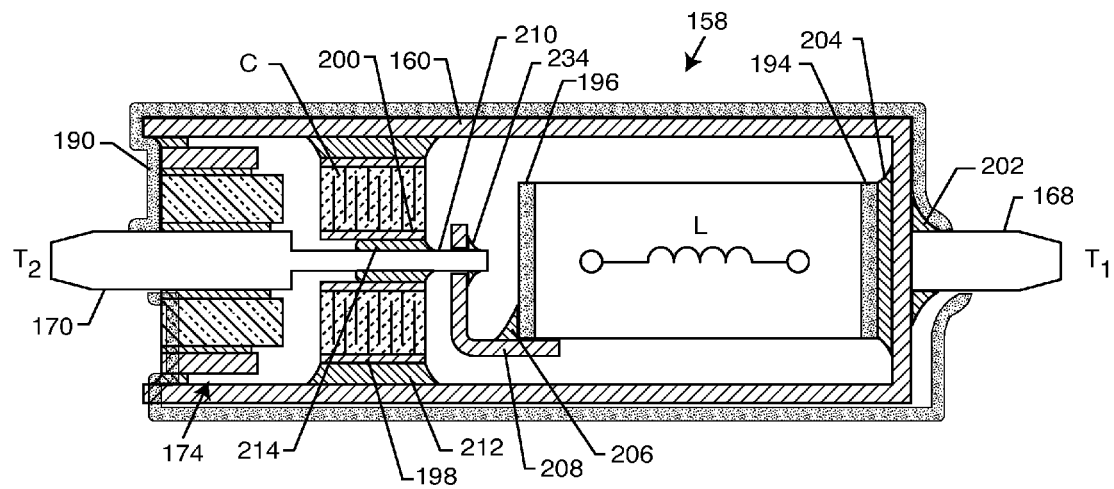
FIG. 27 is a sectional view similar to FIG. 20, but illustrating an alternative embodiment where the chip capacitor has been replaced with a feedthrough capacitor.
Figure 28:
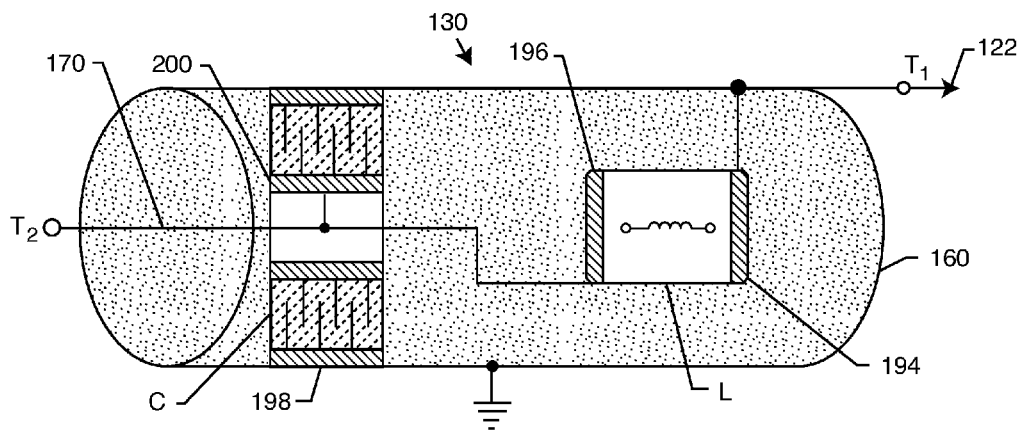
FIG. 28 is a schematic illustration showing electrical connections of the inductor and capacitor relative to the lead.
Figure 29:
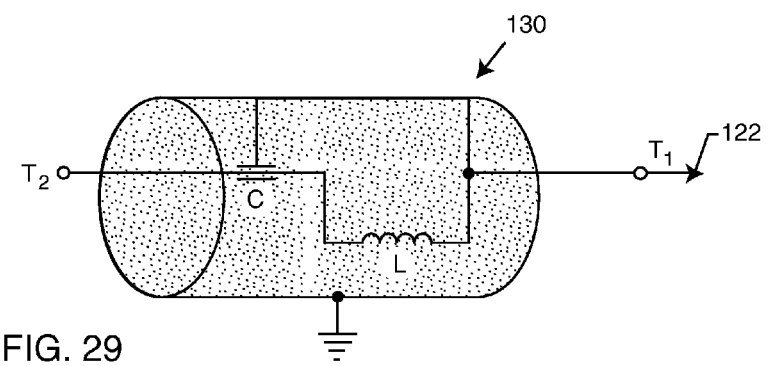
FIG. 29 is an electrical schematic diagram of the structure shown in FIGS. 27 and 28.

FIGS. 27-29 illustrate a configuration where a chip inductor L is physically disposed in series with a feedthrough capacitor C, and yet is electrically connected in parallel to form a bandstop filter 130. The chip inductor L and the feedthrough capacitor C are disposed within an EMI shielded hermetic container 158 comprising a conductive housing 160 of a biocompatible material which includes one open end, and a hermetic seal assembly 174 disposed within the open end of the housing 160. The conductive terminal 168 is conductively coupled to the housing 160 by a laser weld 202. The first conductive termination surface 194 of the inductor L is conductively coupled to the housing 160 by means of a solder, braze, or conductive adhesive 204 or the like. The second conductive termination surface 196 of the inductor L is similarly conductively coupled by means of a solder, braze, or conductive adhesive 206 or the like, to a conductive bracket 208 which is also conductively coupled to an extension 210 of the conductive terminal 170 which extends through a central passageway of the feedthrough capacitor C. The first conductive termination surface 198 of the capacitor C is conductively coupled to the housing 160 by means of conductive adhesive 212 or the like, and the second conductive termination surface 200 of the feedthrough capacitor C is conductively coupled to the extension 210 of the conductive terminal 170 by means of conductive adhesive 214 or the like. The hermetic seal assembly 174 disposed within the opening to the housing 160, and which prevents direct contact between body fluids and the inductor L, the capacitor C and related electrical components, is essentially the same as the hermetic seal assembly 174 illustrated in FIGS. 20-23. The illustrated structure advantageously eliminates one hermetic seal assembly in comparison with previously illustrated embodiments, by providing a terminal 168 which is shorted to the conductive EMI shield housing 160. As shown, the optional conformal coating 190 is applied over the entire outer surface of the housing 160 as well as a portion of the terminals 168 and 170. This conformal coating 190 advantageously provides additional electrical isolation between the two terminals 168 and 170.

Figure 30:
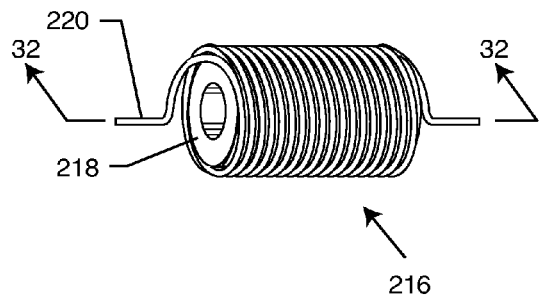
FIG. 30 is a perspective view of a solenoid inductor wrapped around a non-ferromagnetic core.
Figure 31:
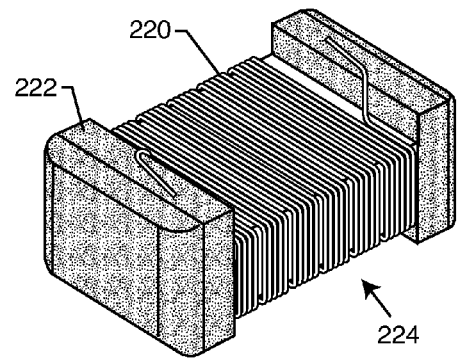
FIG. 31 is similar to FIG. 30, showing inductor wires coiled around a plastic support structure to form the equivalent of an air-wound inductor.
Figure 32:
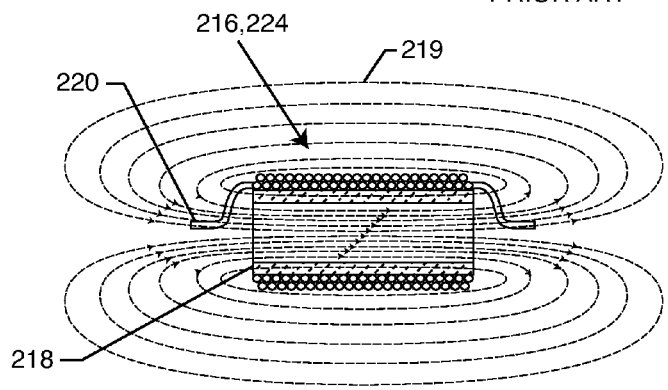
FIG. 32 is a sectional view taken along the line 32-32 from FIG. 30, illustrating the magnetic field when no shield is present.

FIG. 30 illustrates a solenoid inductor 216 wrapped around a non-ferromagnetic core 218. The term solenoid inductor as defined herein includes any inductor geometry whose magnetic fields 219 are aligned generally along the central axis of the lead and/or the shield 126. The inductor 216 consists of coils of wire 220 which can be single or multi-layer as illustrated in cross-section in FIG. 32. The inductor 216 may be wound on a magnetic material such as a ferrite core, however, this is highly undesirable for MRI applications. This is because the MRI main static field would tend to saturate such high permittivity (k) ferrite materials. Accordingly, the shielded inductors of the present invention are generally comprised of air or non-ferromagnetic materials as shown in FIG. 31, where the inductor wires 220 are coiled around a support structure 222 of a non-magnetic material, such as a ceramic or plastic. This makes the coil 224 of FIG. 31 equivalent to an "air-wound" inductor. These so-called air coils are not very volumetrically efficient and tend to have a magnetic field 219 as illustrated in FIG. 32. This is well known in physics and for a DC case, would generate a north and south pole. In an AC case, which is the case for an MRI RF application, these field lines would be alternating at the RF frequency of the MRI RF pulsed field. These field lines 219 would therefore build up and collapse which also reverses the induced currents again at the frequency of the RF pulsed field. The inventors have determined that the field lines 219 of the solenoid inductors 216, 224 are affected when the inductor is placed inside of an electromagnetic interference shield 126. As previously described in connection with FIGS. 20 and 27, this electromagnetic interference shield 126 can also be the housing 160 of a hermetically sealed container.

Figure 33:
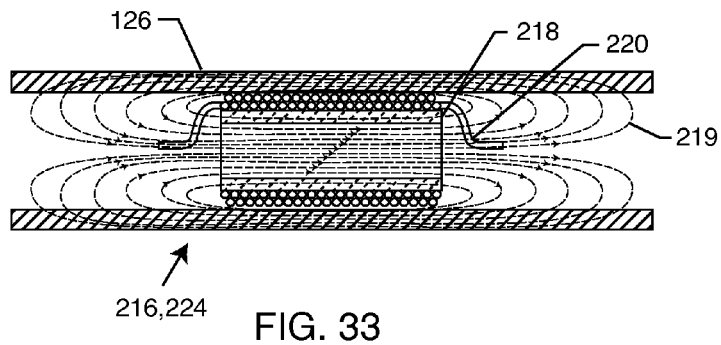
FIG. 33 is similar to FIG. 32, illustrating changes in the magnetic field when the inductor is shielded.

As one can see in FIG. 33, when the solenoid inductor 216, 224 is placed within a conductive shield 126, the magnetic field lines 219 of the solenoid inductor coil 220 tend to capture and induce currents in the shield 126 which affects the energy stored in the coil's magnetic field, and therefore the inductance value of the inductor 216, 224. FIG. 33 illustrates a worst case for a solenoid coil's magnetic fields 219 wherein the shield 126 has a very high permeability. The high permeability of the shield 126 creates a low reluctance path for the magnetic fields 219 which tends to capture some amount of the coil's magnetic field 219 in the shield 126. The amount of flux captured by the shield 126 is directly related to the material's permeability; as the permeability increases, more magnetic field lines 219 tend to be captured within the shield. In a preferred embodiment, the shield 126 is of a biocompatible material such as platinum-iridium alloy which has a relatively low permeability. Accordingly, for a shield 126 of platinum-Iridium (or equivalent biocompatible metals such as titanium, stainless steel, niobium), the magnetic field lines 219 do not completely collapse into the shield walls as shown in FIG. 33., but rather the field lines 219 penetrate and propagate outside the shield 126. For both high permeability and lower permeability shields 126, the value of the solenoid coil inductance in nanoHenries or microHenries is shifted when one measures this value with the inductor coil 220 outside of the shield 126 (in air) as opposed to inserting the inductor coil 220 into the shield. When the inductor 216, 224 is a component of an L-C bandstop filter 128, 130, it is very critical that this change in inductance be accounted for in the design. If it is not properly accounted for, the resulting resonant frequency of the L-C bandstop filter 128, 130 may not be centered on an MRI band of RF pulsed frequencies.

Figure 34:
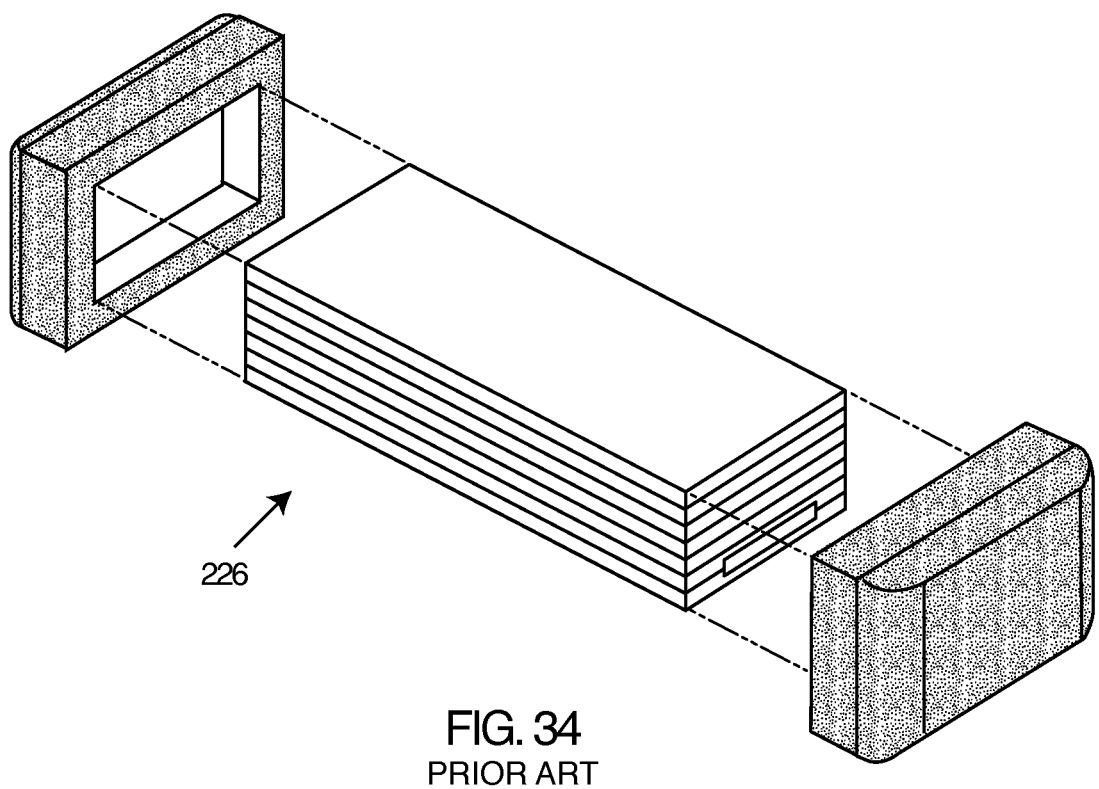
FIG. 34 illustrates a thick film inductor.

FIG. 34 illustrates a prior art thick film or chip inductor 226 taken from U.S. Pat. No. 5,970,604, the contents of which are incorporated by reference. As defined herein, the term "chip inductor" includes any inductor winding or circuit trace geometry whose magnetic fields are generally aligned at 90 degrees to the central axis of the lead 114 and/or the shield 126. Such chip or thick film inductors 226 may be utilized in connection with the present invention, either alone or in connection with a parallel capacitor C to form a bandstop filter 128, 130.

Figure 35:
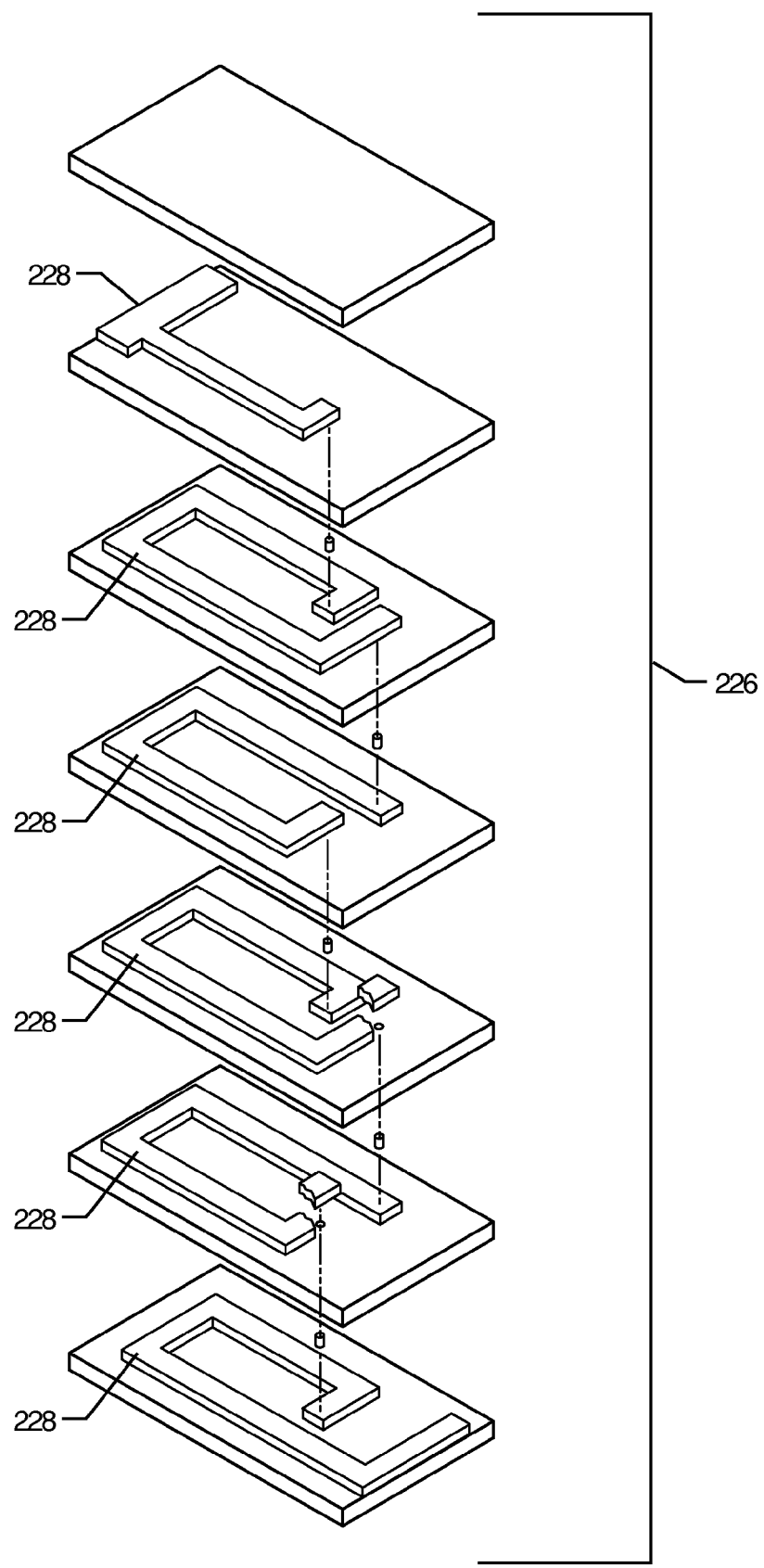
FIG. 35 shows the arrangement of circuit traces that form the thick film inductor of FIG. 34.

FIG. 35 shows an exemplary arrangement of circuit traces 228 that form the thick film inductor 226. The electromagnetic field lines of such an inductor are generally opposite orthogonally to those for the solenoid inductors of FIGS. 30 and 32.

Figure 36:
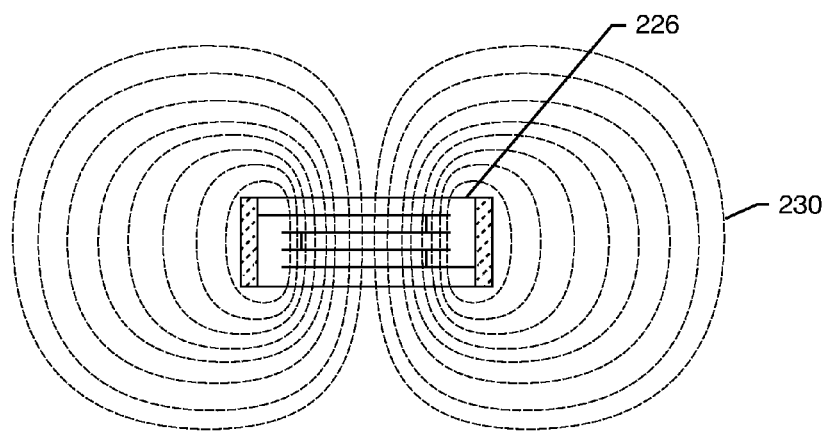
FIG. 36 is similar to FIG. 32, illustrating electromagnetic field lines for the thick film inductor when not shielded.

FIG. 36 illustrates the ideal (in air) electromagnetic fields 230 around the thick film inductor 226 of FIGS. 34 and 35. In this case, the magnetic fields 230 are directed at 90 degrees to the direction of the implanted lead center line. When this type of thick film inductor 226 is inserted into a shielded housing 126, the field lines will induce currents into the surrounding electromagnetic shield as shown in FIGS. 37 and 38.

Figure 37:
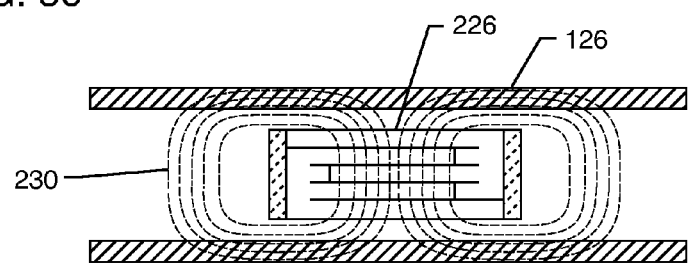
FIG. 37 is similar to FIG. 33, illustrating changes in the magnetic field lines when the thick film inductor is shielded.
Figure 38:
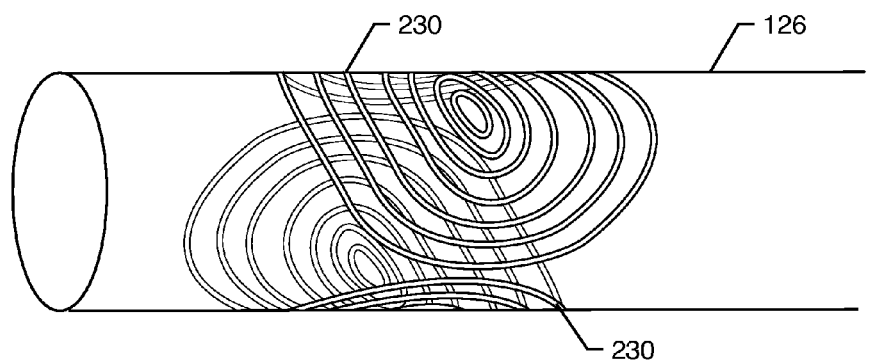
FIG. 38 illustrates distribution of current induction for a thick film inductor when shielded.

FIGS. 37 and 38 illustrate how the magnetic fields 230 of the chip inductor of FIGS. 34 and 35 tend to be captured and induce currents into the shield walls 126 which affects the energy stored in the coil's magnetic field and the coil inductance value. FIG. 37 is a worst case for a chip inductor's magnetic fields 230 wherein the shield 126 has a very high permeability. The high permeability of the shield creates a low reluctance path for the magnetic fields 230 of the inductor 226 which tends to capture a great deal of the coil's magnetic field 230 in the shield walls 126. FIG. 38 comes from electromagnetic field modeling and shows the magnetic field pattern 230 of the chip inductor 226 which is orthogonal to the both central axis of the shield 126 and the lead central axis. In a preferred embodiment, the shield 126 is of a biocompatible material such as platinum-iridium alloy which has a relatively low permeability. Accordingly, for a shield 126 of platinum-Iridium material (or equivalent biocompatible metals such as titanium, stainless steel, niobium), the magnetic field lines 230 do not completely collapse into the shield walls 126 as shown in FIG. 37, but rather the field lines 230 penetrate and propagate outside the shield 126. For a chip inductor 226 inserted inside of either a high permeability or lower permeability shield 126, the value of the inductance in nanoHenries or microHenries is different if one measures this value with the inductor outside of the shield 126 (in air) as opposed to inserting the inductor into the shield. This shift is less than that for a solenoid inductor 216, 224, but is still significant. Still, when the chip inductor 226 is a component of an L-C bandstop filter 128, 130, it is very critical that this change in inductance be accounted for in the design. If it is not properly accounted for, the resulting resonant frequency of the L-C bandstop filter 128, 130 may not be centered on an MRI band of RF pulsed frequencies which would make it ineffective.

In general, the amount of induced current from the magnetic field 230 of a chip inductor 226 in the shield 126 encompasses less area and less magnitude as compared to the solenoid inductors 216, 224 of FIGS. 31-33. In other words, there is less energy loss and inductive shift from a chip inductor geometry as compared to a solenoid inductor type of arrangement.

Figure 39:
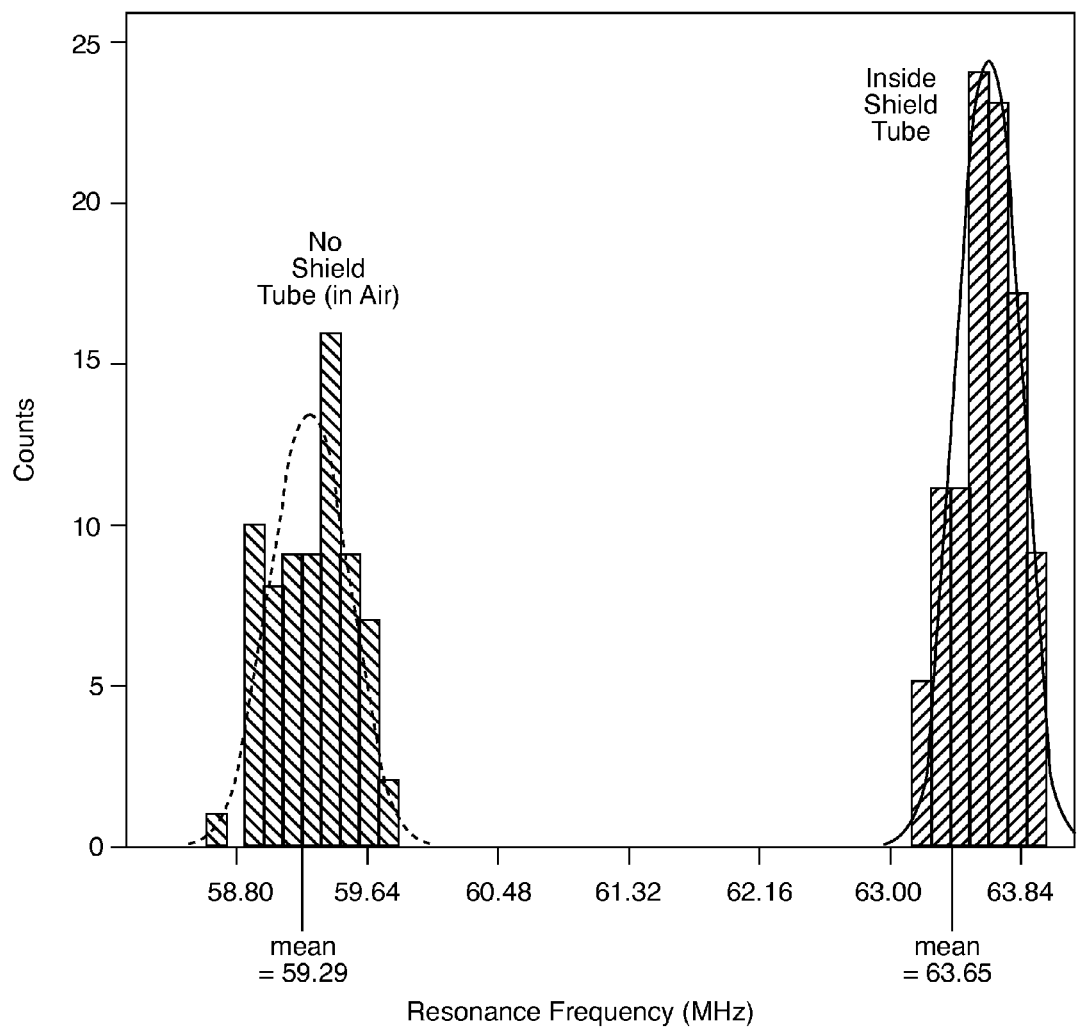
FIG. 39 is a graph of histograms from various prototypes of solenoid inductors.

FIG. 39 is a graph of histograms from various prototypes of solenoid inductors that were built as a component of L-C resonant bandstop filters. A network analyzer was used to measure the resonant frequency of the bandstop filter within the limit of the component tolerances of the inductors and capacitors. The left hand histogram is a graph of the L-C bandstop filter resonant frequencies measured with the bandstop filter disposed well outside of the overall EMI shield 126 (in other words, in air). The mean resonant frequency was measured to be 59.29 MHz with a standard deviation of 0.2486 based on 71 units measured. Then the bandstop filters were placed inside of a shielded housing 126 and again their resonant frequencies were measured. In this case the mean resonant frequency was determined to be 63.65 MHz with a standard deviation of 0.1958 with a total of 100 samples measured. In all cases, the capacitors were 15.9 picofarad and mounted on circuit boards similar to those shown in FIG. 24. In this case, the shielded housing was made of platinum-iridium. Remarkably, this effect on the inductor fields accounts for a shift in resonant frequency of the bandstop filter of 4.3 MHz or 6.8%. The frequency of resonance $f_r$ for a bandstop filter is given in FIG. 16 where one can see there is an inverse relationship between the square root of the inductance and capacitance and the resonant frequency. Assuming the capacitance is held constant at 15.9 picofarads and solving the resonant frequency equation for inductance, this means that the inductance in air on average was 453.2 nanoHenries and dropped to an effective 394.3 nanoHenries when inserted into the surrounding EMI shield housing 126. This is an average shift of 58.9 or approximately 59 nanoHenries, which is about a 13% shift in the inductance value. Accordingly, in order for the L-C bandstop filter to be properly resonant in an MRI RF pulsed center frequency, this shift in the inductance in air versus insertion into the MRI shield 126 must be properly accounted for. There are many variables that come into play in this calculation, including the physical properties of the inductor, its orientation as a solenoid or a chip inductor, the thickness and diameter of the surrounding electromagnetic shield and its high frequency material properties, including its high frequency resistance.

Figure 40:
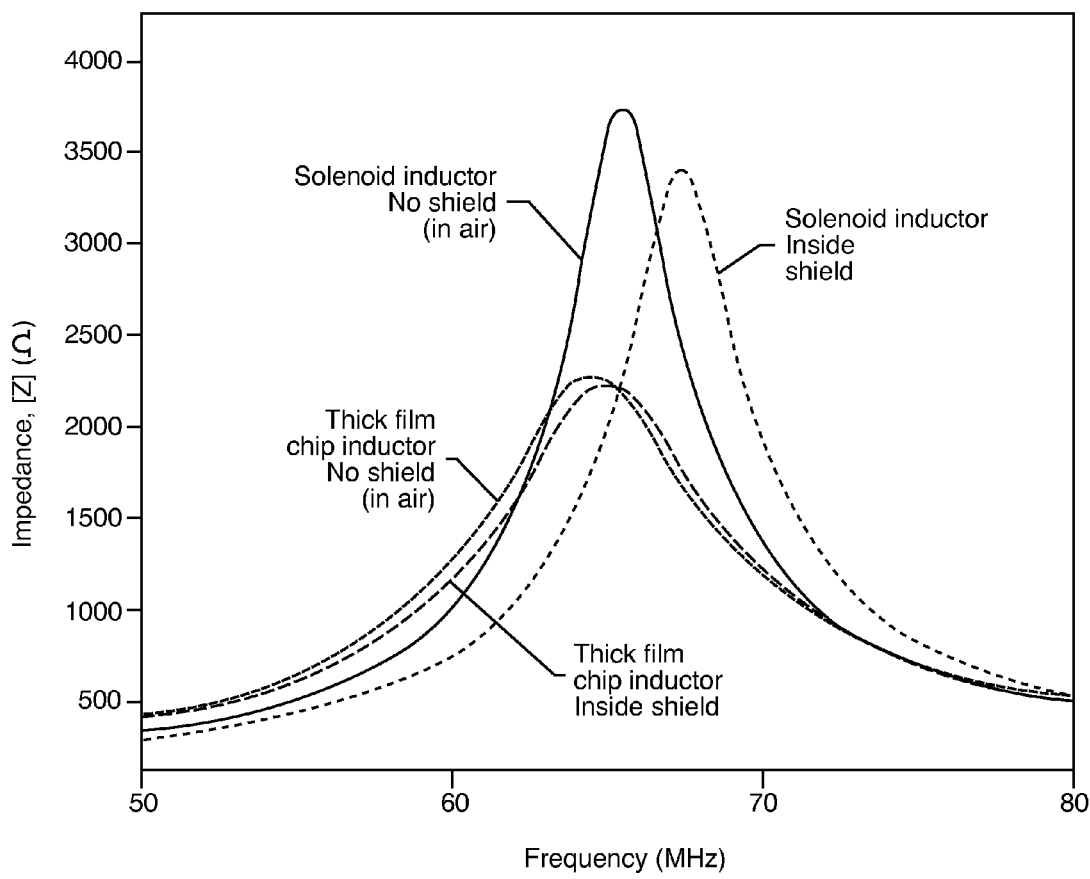
FIG. 40 is a graph of impedance versus frequency curves for circuits boards with either thick film chip or wire wound or solenoid inductors, when shielded in comparison to when not shielded.

FIG. 40 illustrates impedance versus frequency curves for circuit boards with either thick film chip or wire wound or solenoid inductors (the central axis and corresponding magnetic fields of a typical thick film inductor are oriented at 90 degrees to a typical wire wound solenoid inductor). This graph demonstrates the effect of placing the thick film or wire wound inductor inside a cylindrical metal shield tube 126. Notice that the solenoid-type wire wound inductor boards exhibit a significant shift in resonant frequency and impedance. Having a very high impedance at resonance is desirable to prevent undesirable MRI RF induced currents from flowing into surrounding body tissues.

Figure 41:
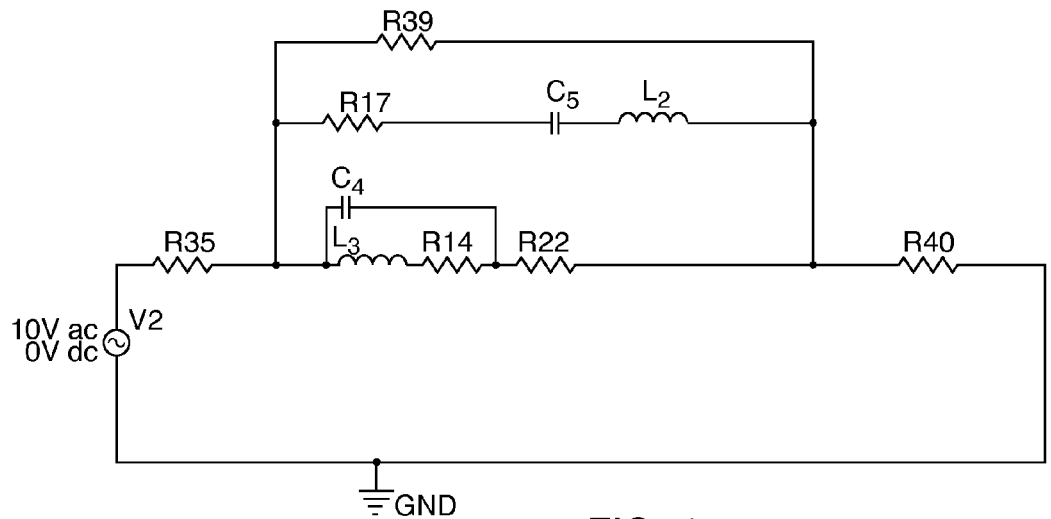
FIG. 41 is a PSPICE computer model for predicting the resonant circuit behavior of a solenoid inductor in air.
Figure 42:
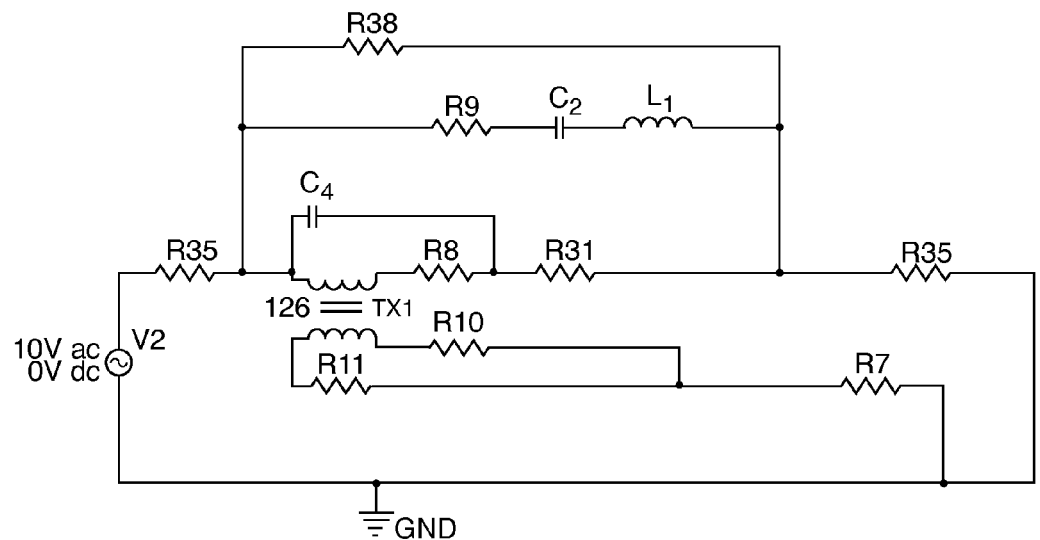
FIG. 42 is a PSPICE computer model similar to FIG. 41, modified to add mutual inductance coupling to a surrounding electromagnetic shield.

FIG. 41 is a PSPICE computer model developed by the inventors to be able to predict the resonant circuit behavior of a solenoid inductor in air. This model was modified as shown in FIG. 42 to add mutual inductance coupling to a surrounding electromagnetic shield 126. This PSPICE model is used in conjunction with the present invention to predict that amount of resonant shift and the amount of inductive offset one needs to make while designing inductors for shielded L-C bandstop filters.

Figure 43:
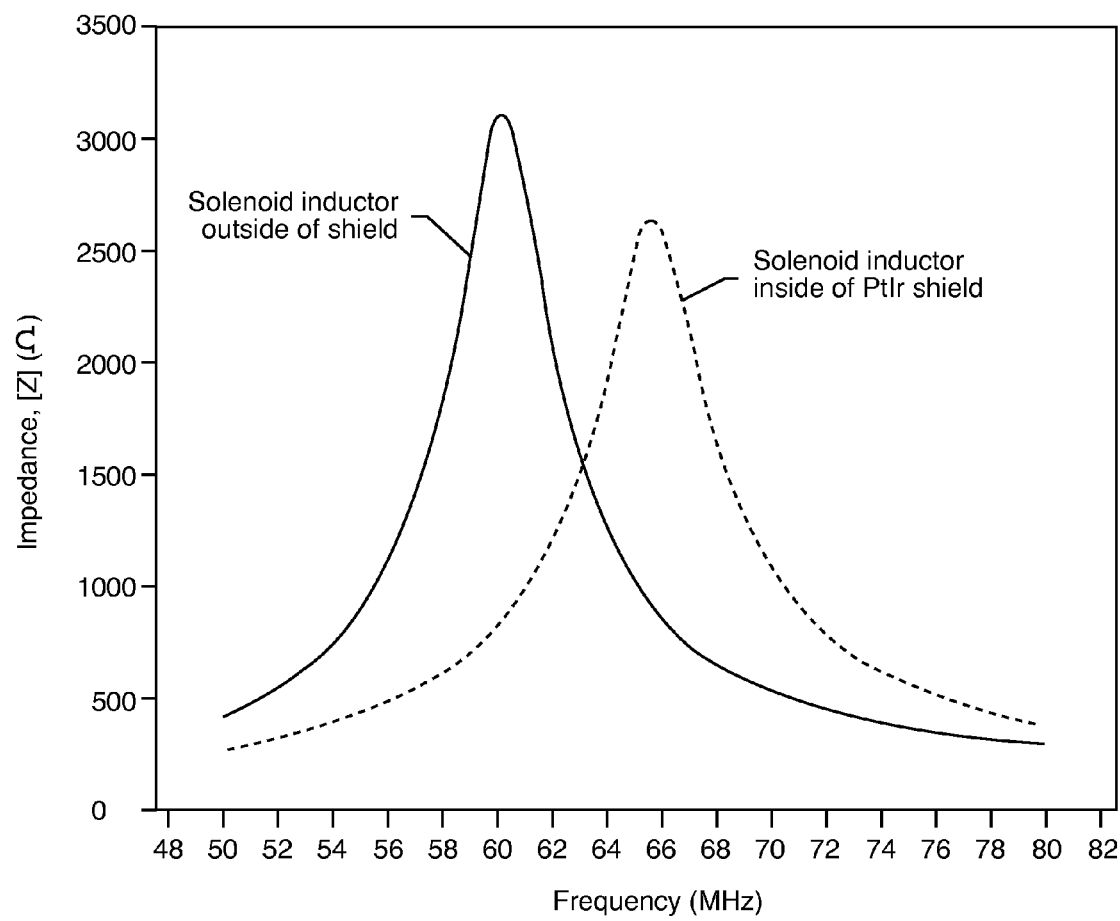
FIG. 43 is a graph of the frequency response predicted by the PSPICE models of FIGS. 41 and 42.

FIG. 43 is the frequency response predicted by the PSPICE models for the inductor inside and outside of a platinum-iridium shielded housing. As one can see, the PSPICE model very accurately fits the empirical data previously plotted in FIG. 40.

The PSPICE model can be used to adjust a first inductive value with the inductor outside of a shielded housing so that a second inductive value with the inductor inside of a shielded housing has the proper value. For example, in a resonant tuned L-C bandstop filter it is very important that the inductor value and the capacitor value have a fairly tight tolerance so that the resulting resonant frequency occurs in the center of a range of MRI RF pulsed frequencies.

Figure 44:
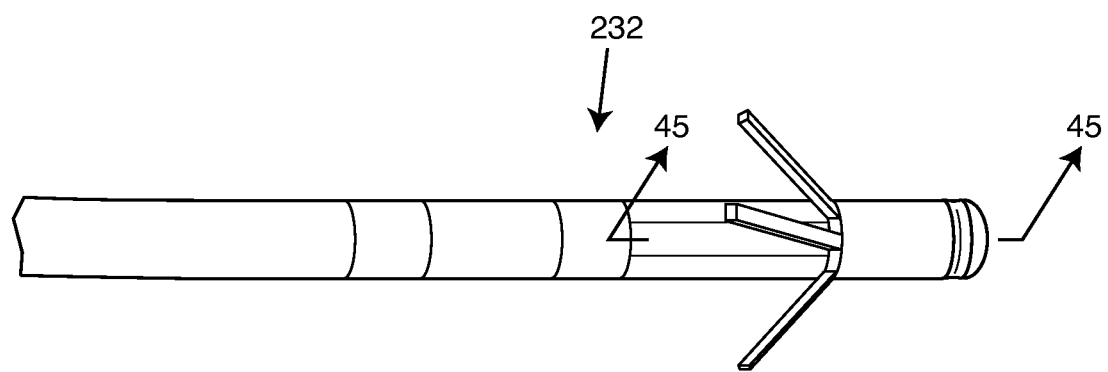
FIG. 44 is a perspective view of a passive electrode fixation tip typically used in cardiac pacemaker applications.

With reference now to FIG. 44, a passive electrode fixation tip 232 typically used in cardiac pacemaker applications is shown in which the shielded inductor, passive network or bandstop filter assembly of the present invention can be incorporated.

Figure 45:
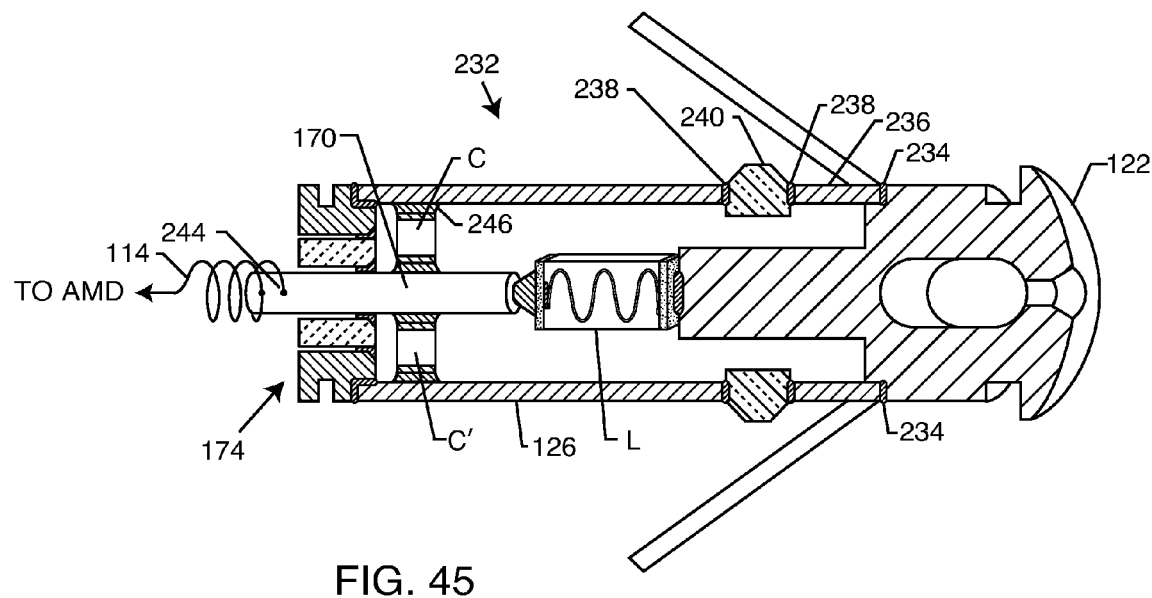
FIG. 45 is an enlarged sectional view taken generally along line 45-45 from FIG. 44.

FIG. 45 is a sectional view of a portion of the passive electrode 232 taken along the line 45-45 from FIG. 44, and illustrates a hermetically sealed package consisting of a passive distal tip electrode 122 which is designed to be in intimate contact with body tissue, such as inside the right atrium of the heart. A hermetic seal is formed at laser weld 234 as shown between the tip electrode 122 and a metallic ring 236. Gold brazes 238 are used to separate the metallic ring 236 from the shield surface 126 by use of an intervening insulator 240. This insulator 240 could typically be of alumina ceramic, other types of ceramic, glass, sapphire or the like. The 126, which also acts as an energy dissipating surface EDS, is typically gold brazed to the other side of the insulator 240 as shown. An inductor L, such as an inductor chip is shown connected between the distal tip electrode 122 and a terminal pin 170 which is attached as by laser welds 244 to the end of the lead 114 extending through the body to the AMD. As shown, terminal pin 170 protrudes through a hermetic seal assembly 174.

The shield/energy dissipating surface 126 of FIG. 45 is typically of a biocompatible metal, such as titanium, platinum or the like. It is important that the shield/energy dissipating surface 126 be both electrically conductive and thermally conductive so that it can transfer RF and thermal energy into body fluid or tissue. The shield/energy dissipating surface 126 can be roughened or even corrugated or bellowed to increase its surface area and therefore its energy dissipating properties into surrounding body fluids or body tissue.

Figure 47:
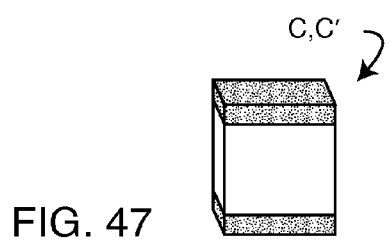
FIG. 47 is a perspective view of a typical off-the-shelf commercial monolithic ceramic capacitor (MLCC)

Capacitive elements C and C' shown in FIG. 45 are designed to act as a low impedance at higher frequencies. Electrical connections 246 couple the capacitor C to the shield/energy dissipating surface 126. This forms a broadband low pass filter wherein the inductor L acts in cooperation with the capacitive elements C and C'. The presence of the inductor L enhances the performance of the capacitor elements C and C', which are typical off-the-shelf commercial monolithic ceramic capacitors (MLCCs) such as those illustrated in FIGS. 47 and 48.

An advantage in using a capacitor C as a selective frequency element is that it tends to act as a broadband filter which will attenuate a range of MRI frequencies. For example, placement of an effective capacitor C could attenuate 64 megahertz, 128 megahertz and higher MRI frequencies. However, if one were to use an L-C series trap filter as shown in FIG. 8, then this would only be effective at one MRI frequency, for example 64 megahertz only. Of course, as already been disclosed herein, one could use multiple L-C trap filters. However, in a preferred embodiment the use of a capacitor as is desirable because with a two-element L-type low pass filter, one can attenuate a broad range of MRI RF pulsed frequencies.

Figure 46:
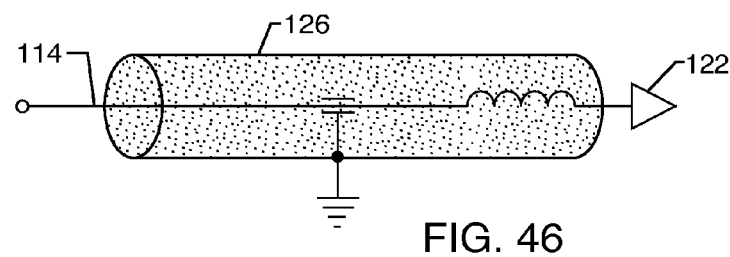
FIG. 46 is an electrical schematic diagram for the circuit of FIG. 45.

The schematic diagram for the circuitry of FIG. 45 is shown in FIG. 46. Capacitors C and C' are actually in parallel and act as a single capacitive element. The reason for multiple capacitors is to obtain a high enough total capacitance value so that the capacitive reactance is very low at the frequency of interest (for example, 64 MHz for a 1.5 T MR system).

Figure 48:
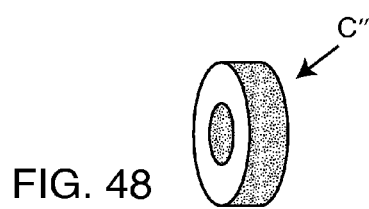
FIG. 48 is a perspective view of a typical off-the-shelf commercial unipolar feedthrough capacitor.

An alternative capacitor C" for use in the circuit of FIG. 45, known as a unipolar feedthrough capacitor, is shown in FIG. 48. It has outside diameter and inside diameter termination surfaces and for electrical contact. Feedthrough capacitors can be unipolar or multipolar. These are completely described in the prior art; for example, refer to U.S. Pat. Nos. 7,363,090, 4,424,551; 5,333,095; and 6,765,779.

Figure 49:
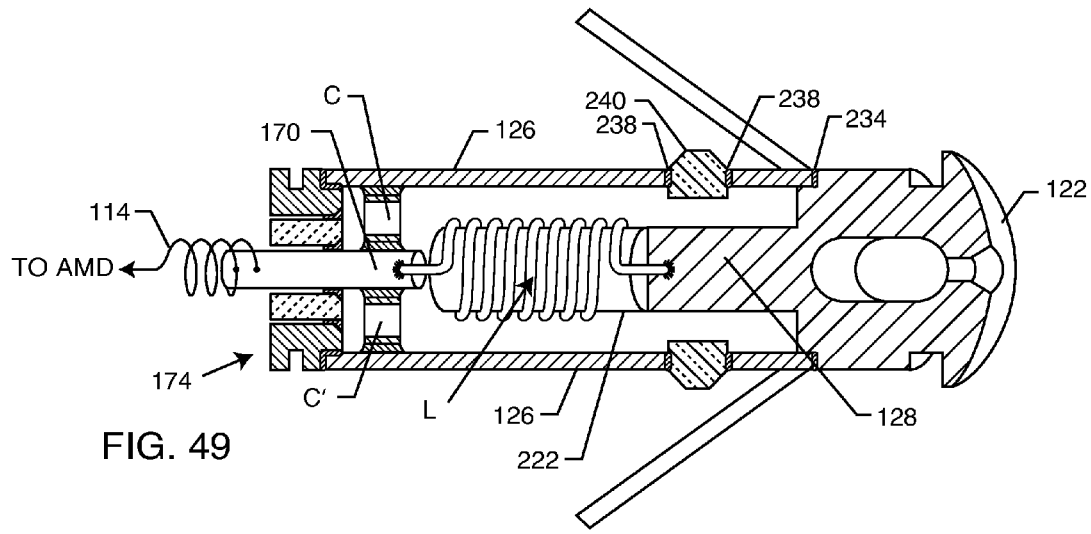
FIG. 49 is a sectional view similar to FIG. 45, except that the inductor element is wire wound around a non-ferromagnetic mandrel.

FIG. 49 is similar to FIG. 45 except that the inductor element L is wire wound around a non-ferromagnetic mandrel 222 (formed from a material such as a ceramic or plastic). This type of solenoid wound inductor L has much higher current handling capability as compared to the inductor chip of FIG. 45. The inductor chip of FIG. 45 can be fabricated from a variety of shapes including Wheeler spirals, thick film inductors, and the like. It is important that the inductor element L be able to handle substantially high currents when it is in series with the lead 114. The reason for this has to do with either ICD applications for shock electrodes or automatic external defibrillation (AED) events. AEDs have become very popular in government buildings, hospitals, hotels, and many other public places. When the external defibrillator paddles are placed over the chest of a cardiac pacemaker patient, the high voltage that propagates through body tissue can induce powerful currents in implanted leads. Accordingly, the inductor L has to be designed to handle fairly high current (as high as the 4 to 8 amp range in short bursts). The wire wound inductor L of FIG. 49 has wire of a larger cross-sectional area and is therefore a higher current handling inductor.

Figure 50:
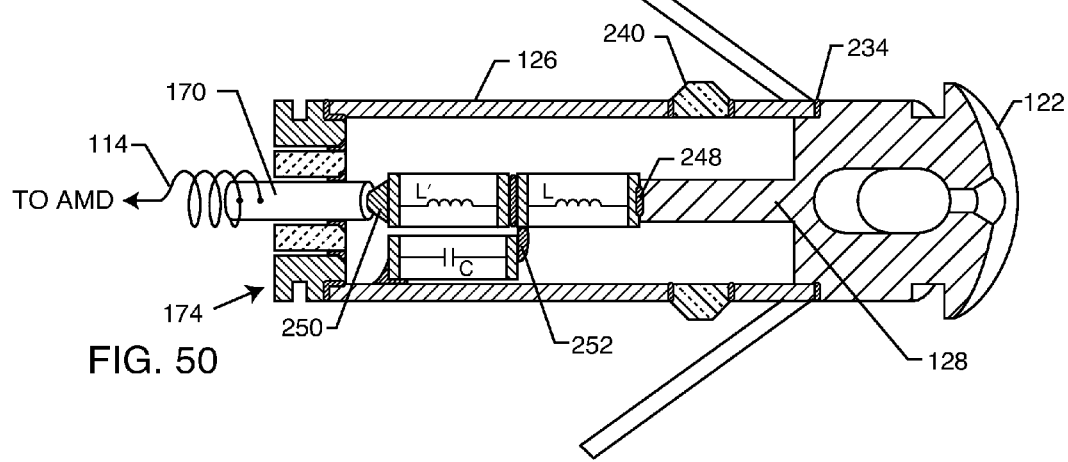
FIG. 50 is a sectional view similar to FIGS. 45 and 49 wherein a pair of inductors are coupled in connection with a capacitor to form a "T" filter within the passive electrode tip.

FIG. 50 illustrates an entirely different approach for the diverting of RF energy away from the electrode tip 122 to the shield/energy dissipation surface 126. Shown is an electrical connection 248 between a first inductor L and the distal tip electrode assembly 122. The other end of the first inductor L is connected to a second inductor L' which is in turn electrically connected at 250 to the hermetic terminal pin 170. The capacitor C is connected between the junction of the two inductors L and L' at electrical connection 252. The other end of the capacitor is electrically connected to the shield energy dissipating surface 126. An insulating sleeve (not shown) can be used to ensure that the capacitor termination and electrical connection 252 does not inadvertently make contact (short out) with the shield/energy dissipating surface 126.

Figure 51:
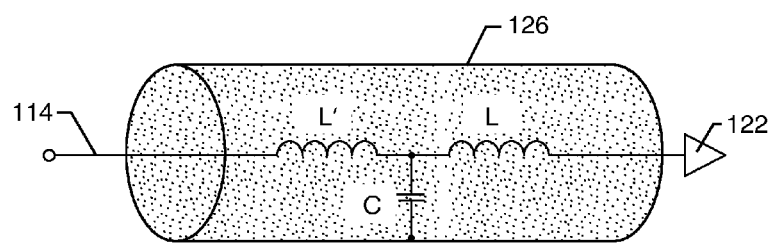
FIG. 51 an electrical schematic for the structure shown in FIG. 50.

The electrical schematic for FIG. 50 is shown in FIG. 51. This forms a low pass filter (in this example, a T filter), which tends to enhance the filtering performance by directing more of the RF energy to the shield/energy dissipating surface 126. As previously mentioned, a single or multi-element low pass filter would attenuate a broad range of MRI frequencies and would be an advantage in the present invention for that reason. In accordance with the present invention, it is important that the value of the inductance for either the chip inductor L of FIG. 45, the solenoid inductor L of FIG. 49, or the chip inductors L, L' of FIG. 50 have their first inductive values adjusted so that their inductance, when inserted into the overall shield/energy dissipating surface 126, so that the resultant package value is correct.

Figure 52:
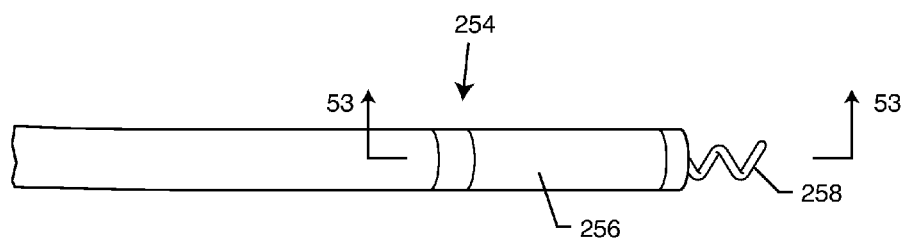
FIG. 52 is a perspective view of a generic prior art active fixation distal tip typically used in conjunction with cardiac pacemakers.
Figure 53:
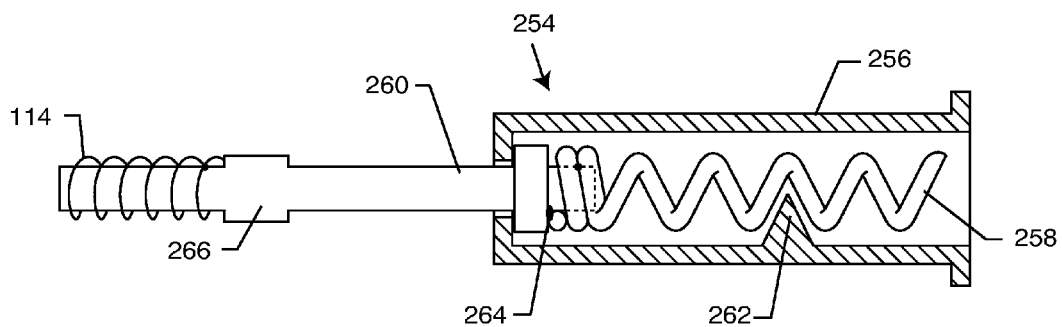
FIG. 53 is an enlarged sectional view taken generally along line 53-53 from FIG. 52.

FIGS. 52 and 53 show a generic prior art active fixation distal tip electrode 254 which is typically used in conjunction with cardiac pacemakers. There is a metallic housing 256 which contains a sharp tipped distal helix coil 258. In FIG. 53, this helix coil 258 is shown in its retracted position, which enables the physician to insert the fixation tip assembly 254 endocardially through the venous system, through the atrium, and through the tricuspid valve into the right ventricle so it does not snag or tear any tissue, and is designed to be extended and screwed into myocardial tissue. Once it is in the appropriate position, the physician then turns leadwire spline assembly 260 in a clockwise rotation. This is done outside the pectoral pocket with the lead 114 protruding from the body. A torque tool is generally applied so that the physician can twist or screw the helix coil 258 into place. Protrusion 262 acts as a gear so that as helix coil 258 is turned, it is screwed forward. This makes for a very reliable fixation into myocardial tissue.

The helix coil 258 is generally attached by a laser weld 264 to an end of the spline assembly 260 as shown. Attached to spline assembly 260, usually by laser welding, is the lead 114 coming from the AMD. An optional feature 266 is placed on spline assembly 260 to create a positive stop as the physician is turning the leadwire assembly and screwing the helix coil 258 into body tissue. Of course, all of the materials of the active fixation tip 254 shown in FIG. 53 are biocompatible. Typically, the helix coil 258 is made of platinum iridium alloy and would be coated with various materials to improve electrical performance. The housing 256 would generally be composed of titanium or another equivalent biocompatible alloy. The spline 260 is generally a platinum iridium alloy.

Figure 54:
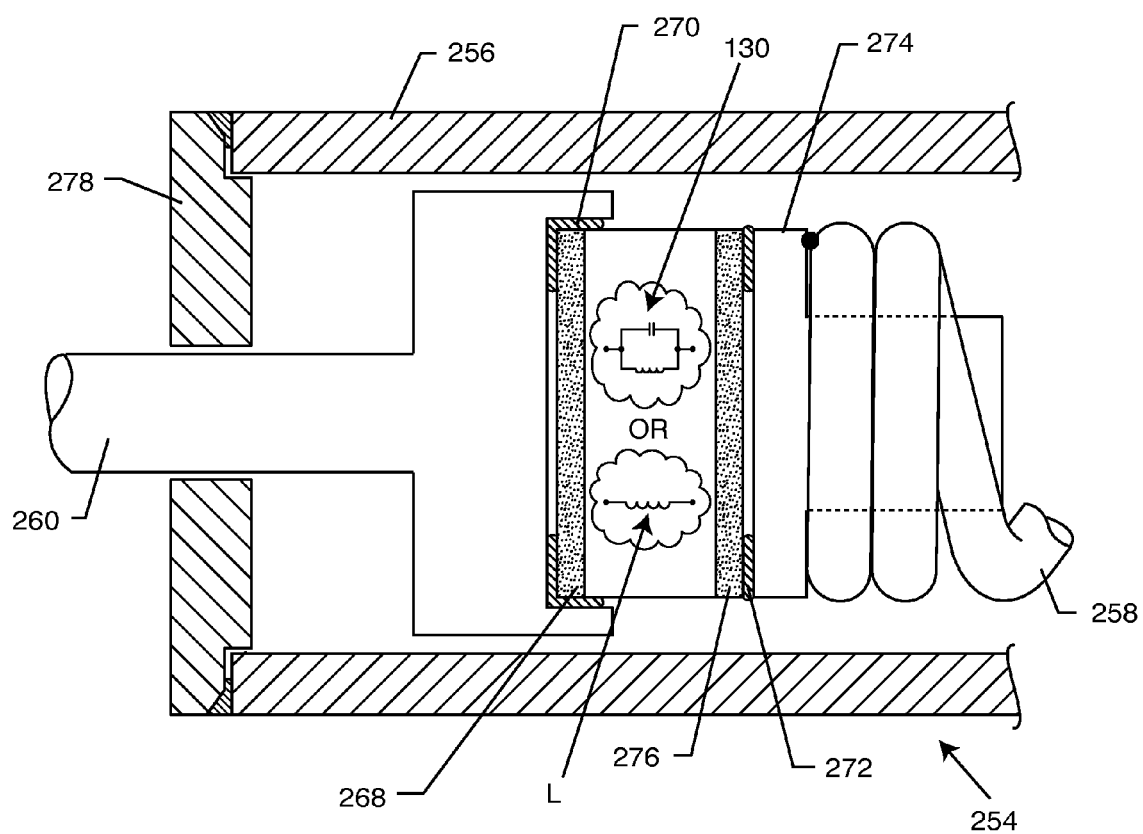
FIG. 54 is a fragmented sectional view of a portion of the active fixation tip of FIGS. 52 and 53, modified to include a shielded inductor or bandstop filter in accordance with the present invention.

FIG. 54 illustrates applying a shielded inductor L or a bandstop filter 130 to the active fixation distal tip 254 shown in FIG. 53. One can see the attachment from the metallization 268 of inductor L or bandstop filter 130 shown attached to the spline 260. This is typically accomplished by a gold braze preform 270. In this case, the spline 260 has been counterbored to receive the end of inductor L or bandstop filter 130. This allows the gold braze material 270 to angle up along the sides of the assembly, thereby adding shear strength. A similar gold braze preform 272 is used to attach a distal tip helix pedestal 274 to the metallization 276 of the inductor or passive network assembly. Of particular advantage is that the assembly illustrated in FIG. 54 can be constructed entirely of low k, very high strength ceramics. In this case, pure alumina or porcelain would be preferred embodiments. These have the advantage of being mechanically very rugged and also very rugged to thermal shock such that it would take pure gold brazing. By use of all biocompatible materials, the assembly is greatly simplified in that it need not be hermetic. It would also be possible to replace the gold brazes 270 and 272 with equivalent laser welds. One can see that the end cap 278 has been modified in a novel way such to make it flush with the outside diameter of the housing 256. This allows one to increase the inside diameter allowing room for the counterbore in the spline assembly 260. The metallic end cap 278 has been stepped so that it is seated for convenient fixturing. The overall housing 256 for the translatable helix assembly 254 is conductive and forms a shield in accordance with the present invention around either the inductor L or the bandstop filter 130. Of course, the inductor L or bandstop filter 130 could be replaced with any low or high pass filter and/or active electronic circuit.

Figure 55:
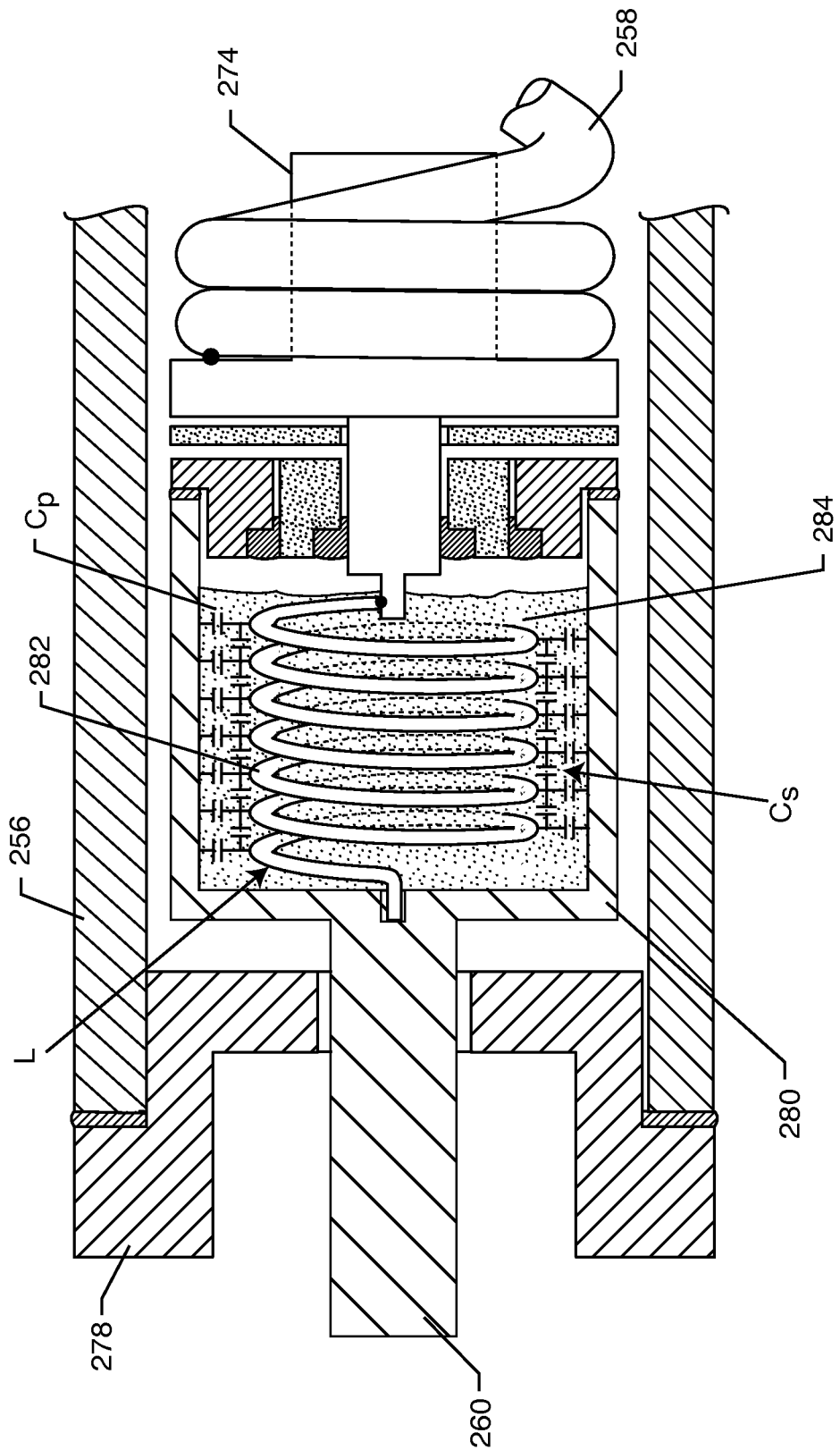
FIG. 55 is a sectional view similar to FIG. 54, where an inductive coil is disposed within a dielectric material such that parasitic capacitances form, with the inductor coil itself, a bandstop filter.

FIG. 55 is an adaptation of the generic prior art active fixation distal tip 254 illustrated in FIG. 54. The design allows: 1) body fluid to freely penetrate to all surfaces interior to the active fixation distal tip 254; and 2) torque experienced by the helix 258 is not transmitted to any electronic component, such as the hermetically sealed bandstop filter 130 and its associated electrical and mechanical connections. The spline shaft 260 has been modified such that it has a relatively long, hollow cylindrical cup portion 280 which allows for installation of the inductor L or bandstop filter 130 inside of it. As will be seen, this will offer a number of important mechanical and biocompatibility advantages. The inductor coil 282 has either been wound around a mandrel which has been removed or is wound around a mandrel which is non-ferromagnetic. In the preferred embodiment, the coil 282 is free standing and is then backfilled with an insulative dielectric material 284. The dielectric insulating material 284 is preferably dispensed as a thermal-setting liquid. After curing at high temperature, the insulating material 284 is cured to form a solid. This material can be a thermal-setting non-conductive epoxy or polyimide or the like. An alternative (not shown) would be to insert a rigid insulating sleeve around the inductor, which has a pre-formed shape. This could be used in combination with insulated inductive wire turns to control the series and parallel parasitic capacitance. The space in between the turns of the coil 282 and its relationship to the cup assembly 280 is important as parasitic capacitances Cp and Cs are developed.

Figure 56:
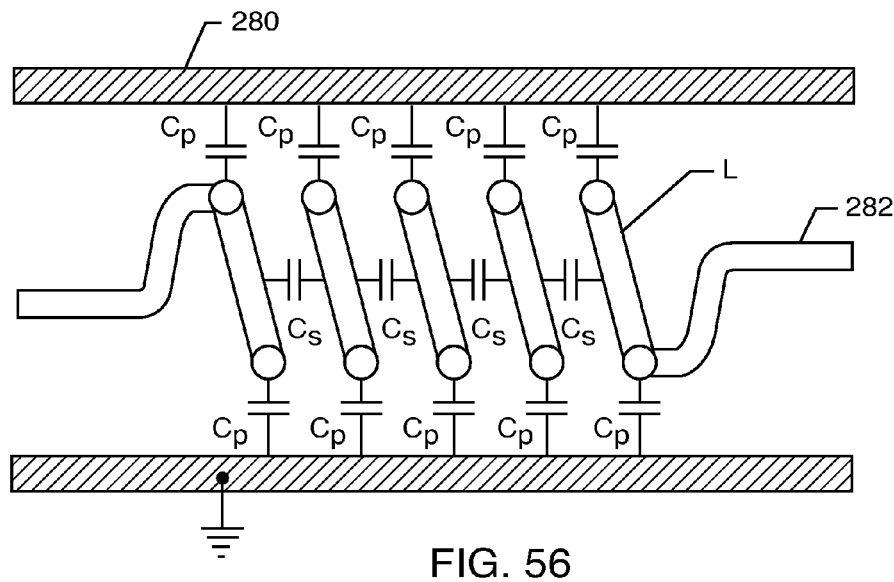
FIG. 56 is an equivalent cross-section schematic diagram for the structure shown in FIG. 55.
Figure 57:
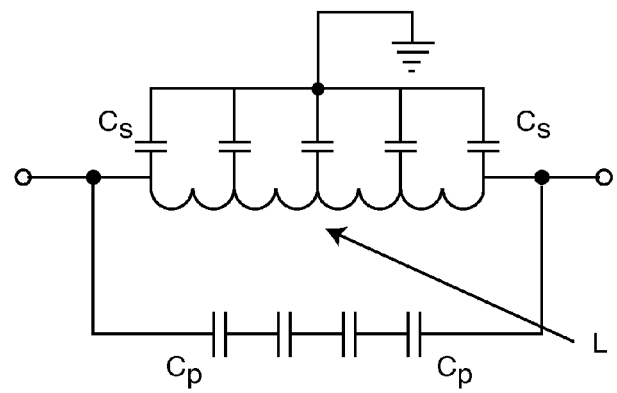
FIG. 57 is an electrical schematic for the structure shown in FIGS. 55 and 56.
Figure 58:
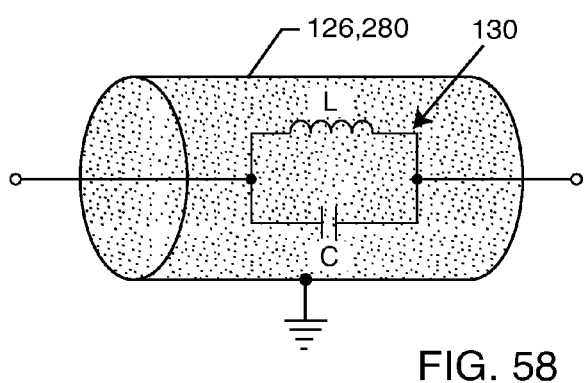
FIG. 58 is a simplified electrical schematic of the structure shown in FIGS. 55-57.

This arrangement is best understood by looking at the equivalent cross-sectional schematic diagram illustrated in FIG. 56. One can see that there are parasitic capacitances Cs formed between the coil turns and also parasitic capacitances Cp to the outer shield housing cup assembly 280. As shown in the schematic in FIG. 57, all of these capacitances add up to form a capacitance in parallel with the inductor L. Once the schematic of FIG. 57 is simplified, it becomes a shielded parallel resonant bandstop filter 130 as shown in FIG. 58.

An additional advantage of having the inductor L or capacitor-inductor 130 inside the housing 256 of the active fixation tip 254 is that this provides a substantial degree of protection to these delicate electronic components. Doctors and other medical personnel are often notorious in the way they handle lead systems. Things can get dropped, moved or placed against them.

FIG. 59 illustrates a reinforced polyimide tubing 286. The typical construction consists of a substrate layer 288, a braided or coiled metallic shield layer 290 and an exterior layer 292 (see cross-section FIG. 60). The substrate 288 and exterior layer 292 are insulative wherein the embedded braided or coiled layer 290 is a conductive metal. In a particularly preferred embodiment, the insulative exterior layer 292 would be eliminated such that the conductive shield 290 would be in direct contact with body fluid. Since the conductive shield 290 has a relatively very large surface area, RF energy can be conducted in the body tissues without resulting in significant temperature rise. This is further described in US 2010/0160997 A1 and US 2010/0023000 A1, both of which are herein incorporated by reference. The most common braid coil 290 material is 304V stainless steel. Other metallic materials can also be used. The embedded braid coil 290 accomplishes RF shielding in accordance with the present invention. FEP and PTFE coatings can be added to the outside diameter both to enhance slickness (lubrication) to make it easy to insert the lead into the body tissues.

FIG. 61 illustrates an alternative embodiment wherein an insulation tube 294 is slipped over the lead 114. Then, a shield layer 290, such as a platinum-iridium, is slipped over the insulation tube 294 as shown.

FIGS. 62 and 63 are similar to FIG. 61 except that the metal shield tube 290 is replaced by wound wire strands 296 or wrapped foil 298, respectively, or other equivalent materials which are commonly used in shielded cables worldwide.

Figure 64:
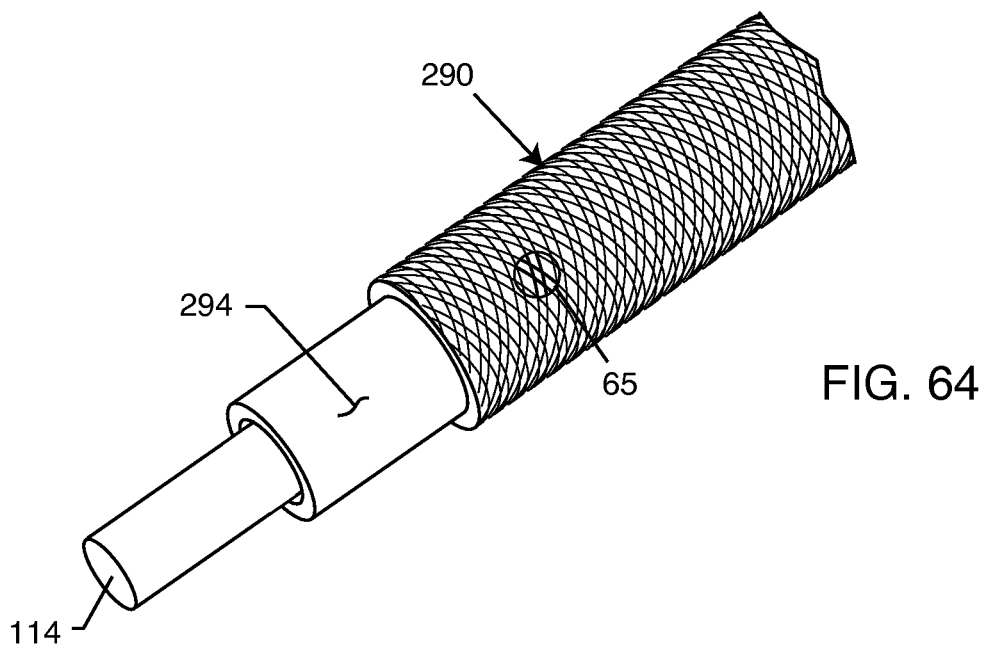
FIG. 64 shows an open mesh cross-braided shield wire instead of the wound shield wire of previous embodiments.
Figure 65:
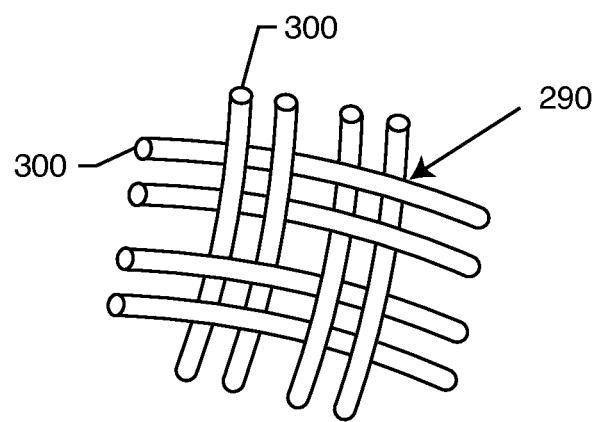
FIG. 65 is an enlarged perspective view of the cross-braided shield of FIG. 64.

FIG. 64 shows an open mesh cross braided shield wire 290 instead of a wound shield wire. The cross braid shield 290 is shown in more detail in FIG. 65, wherein one can see how the braided wires 300 interweave.

The thickness of the conductive shield 290 may require precise control. Thin deposition methods are capable of applying films in the nanometer range. The skin depth or effective skin depth, due to limited conductivity from surface scattering and such, of these thin films may be of a thickness that external electromagnetic waves are not fully attenuated.

Most applications will require full or near-full attenuation to prevent significant currents on the internal sensitive components or connections. However it may be desirable that the energy is not fully attenuated, for example when it is desired to limit the amount of current needed to fully attenuate the incident electromagnetic wave to prevent over-heating. Further, multiple shields may be utilized to prevent overheating or allow limited energy to be attenuated on the internal components to allow monitoring of the external environment for applications such as automatic mode switching or data-logging.

Accordingly, from the foregoing it will be appreciated that the present invention resides in a shielded component or network for an active medical device (AMD) implantable lead which has a length extending from a proximal end to a distal end, all external of an AMD housing. A passive component or network is disposed somewhere along the length of the implantable lead, the passive component or network including at least one inductive component having a first inductive value. An electromagnetic shield substantially surrounds the inductive component or the passive network. Importantly, the first inductive value of the inductive component is adjusted to account for a shift in its inductance to a second inductive value when shielded.

The inductive component may comprise a simple inductor, a low pass filter, an L-C trap, or a bandstop filter. When a bandstop filter or L-C trap filter is provided, the capacitive and inductive components are tuned to impede induced current flow through the implantable lead at a selected center frequency or range of frequencies, technically an MRI RF pulsed frequency or range of RF pulsed frequencies.

Although several embodiments have been described in detail for purposes of illustration, various modifications may be made without departing from the scope and spirit of the invention. Accordingly, the invention is not to be limited, except as by the appended claims.

What is claimed is:

1. An implantable lead configured to be permanently or removably connectable to an active implantable medical device, comprising:
    a) a conductor having a length extending from a proximal end to a distal end;
    b) a distal electrode contactable with biological cells disposed at the distal end of the conductor;
    c) a bandstop filter disposed in series along the length of the conductor, the bandstop filter comprising a self-resonant inductor having an inductance in parallel with a capacitance; and
    d) an electromagnetic shield substantially surrounding the bandstop filter;
    e) wherein the bandstop filter comprises a first resonant center frequency when removed from the surrounding relationship with the electromagnetic shield and a second resonant center frequency when in the surrounding relationship with the electromagnetic shield;
    f) wherein the inductance or capacitance is adjusted to account for a shift between the first and second resonant center frequencies;
    g) wherein the bandstop filter comprises an overall circuit Q wherein the resultant 3 dB bandwidth is at least 10 kHz, such that the bandstop filter
    attenuates RF current flow substantially about the second resonant center frequency.

2. The lead of claim 1 wherein the second resonant center frequency comprises an MRI RF pulsed frequency.

3. The lead of claim 1 wherein the bandstop filter is disposed near, at or within the distal electrode.

4. The lead of claim 1 wherein the electromagnetic shield comprises an energy dissipating surface.

5. The lead of claim 1 wherein the electromagnetic shield is selected from the group consisting of a solid conductor, a wound spiral conductor, a mesh, a tubing, a nanocoating, a conductive heat-shrink tubing, a conductive foil, a wire, a braid, a circuit. trace, a solid tubular material, a conductive polymer, a conductive epoxy, a carbon nano-fiber, a nano-mesh, a nano-coating, and a nano-thread.

6. The lead of claim 1 wherein the electromagnetic shield comprises an open ended tubular or cylindrical shield.

7. The lead of claim 1 wherein the inductance is formed by a discrete passive inductor.

8. The lead of claim 7 wherein the discrete passive inductor is selected from the group consisting of an inductor chip, an inductor winding, an inductor meander, a solenoid inductor or an inductor trace.

9. The lead of claim 1 wherein the capacitance is formed by a discrete passive capacitor.

10. The lead of claim 9 wherein the discrete passive capacitor comprises a chip capacitor or a feedthrough capacitor.

11. The lead of claim 1 wherein the capacitance comprises parasitic capacitance.

12. The lead of claim 1 wherein the bandstop filter inductance is selected from the group consisting of a coiled or spiral inductor, and the capacitance comprises a parasitic capacitance between adjacent turns of the coiled, and spiral inductor.

13. The lead of claim 12 wherein the coiled or spiral inductor comprises a dielectric material surrounding the coiled or spiral inductor, such that adjacent turns of the coiled or spiral inductor are insulated from each other and the shield.

14. The lead of claim 13 wherein the dielectric material has a dielectric constant greater than 1 up to 100.

15. The lead of claim 1 wherein the bandstop filter inductance comprises a coiled or spiral inductor, and the capacitance comprises a parasitic capacitance between the turns of the coiled or spiral inductor and the shield.

16. The lead of claim 1 wherein the shift between the first and second resonant center frequencies is greater than 3.0 mHz or 4.5%.

17. An implantable lead configured to be permanently or removably connectable to an active implantable medical device, comprising:
    a) a conductor having a length extending from a proximal end to a distal end;
    b) a distal electrode contactable with biological cells disposed at the distal end of the conductor;
    c) a bandstop filter disposed in series near, at or within the distal electrode, the bandstop filter comprising a self-resonant inductor, wherein a bandstop filter inductance is formed by an insulated coiled or spiral inductor, and wherein a bandstop filter capacitance comprises a parasitic capacitance between adjacent turns of the insulated coiled or spiral inductor; and
    d) an electromagnetic shield substantially surrounding the bandstop filter;
    e) wherein the bandstop filter comprises a first resonant center frequency when removed from the surrounding relationship with the electromagnetic shield and a second resonant center frequency when in the surrounding relationship with the electromagnetic shield;
    f) wherein the inductance or capacitance is adjusted to account for a shift between the first and second resonant center frequencies;
    g) wherein the bandstop filter comprises an overall circuit Q wherein the resultant 3 dB bandwidth is at least 10 kHz, such that the bandstop filter attenuates RF current flow substantially about the second resonant center frequency.

18. The lead of claim 17 wherein the second resonant center frequency is an MR1 RF pulsed frequency.

19. The lead of claim 17 wherein the electromagnetic shield comprises an energy dissipating surface, 20. The lead of claim 17 wherein the electromagnetic shield is selected from the group consisting of a solid conductor, a wound spiral conductor, a mesh, a tubing, a nano-coating, a conductive heat-shrink. tubing, a conductive foil, a wire, a braid, a circuit trace, a solid tubular material, a conductive polymer, a conductive epoxy, a carbon nano-fiber, a nano-mesh, a nano-coating, and a nano-thread.

21. The lead of claim 17 wherein the electromagnetic shield comprises an open ended tubular or cylindrical shield.

22. The lead of claim 17 wherein the coiled or spiral inductor comprises a dielectric material surrounding the coiled or spiral inductor.

23. The lead of claim 22 wherein the dielectric material has a dielectric constant greater than 1 up to 100.

24. The lead of claim 22 wherein the dielectric material surrounding the coiled or spiral inductor comprises a dielectric wrapping substantially disposed along the entire length of the coiled or spiral inductor.

25. The lead of claim 17 wherein the capacitance further comprises a parasitic capacitance between the adjacent turns of the insulated coiled or spiral inductor and the electromagnetic shield.

26. An implantable lead configured to be permanently or removably connectable to an active implantable medical device, comprising:
   a) a conductor having a length extending from a proximal end to a distal end;
   b) a distal electrode contactable with biological cells disposed at the distal end of the conductor;
   c) a passive electrical component disposed in series along the length of the conductor, the passive electrical component comprising a resonant filter circuit including at least one inductor; and
   d) an electromagnetic shield substantially surrounding the passive electrical component;
   e) wherein the at least one inductor comprises a first inductance value when removed from the surrounding relationship with the electromagnetic shield and a second inductance value when in the surrounding relationship with the electromagnetic shield;
   f) wherein the first inductance value and the second inductance value change a resonant frequency of the passive electrical component;
   g) wherein the passive electrical component comprises an overall circuit Q, wherein the resultant 3 dB bandwidth is at least 10 kHz, such that the passive electrical component attenuates RE pulsed current flow substantially about the resonant frequency resulting from the second inductance value, wherein the resonant frequency comprises an MRI RF pulsed frequency.

27. The lead of claim 26 wherein the electromagnetic shield is selected from the group consisting of a solid conductor, a wound spiral conductor, a mesh, a tubing, a nano-coating, a conductive heat-shrink tubing, a conductive foil, a wire, a braid, a circuit trace, a solid tubular material, a conductive polymer, a conductive epoxy, a carbon nano-fiber, a nano-mesh, a nano-coating, and a nano-thread.

28. The lead of claim 27 wherein the discrete passive inductor is selected from the group consisting of an inductor chip, an inductor winding, an inductor meander, a solenoid inductor, and an inductor trace.

29. An implantable lead, comprising:
   a) a conductor having a length extending from a proximal end to a distal end;
   b) an electrode connectable with biological tissue disposed at the distal end of the conductor;
   c) a bandstop filter disposed in series near, at or within the electrode, the bandstop filter comprising a self-resonant inductor having an inductance in parallel with a capacitance; and
   d) an electromagnetic shield substantially surrounding the bandstop filter;
   e) wherein the bandstop filter comprises a first resonant center frequency when removed from the surrounding relationship with the electromagnetic shield and a second resonant center frequency when in the surrounding relationship with the electromagnetic shield;
   f) wherein the inductance or capacitance is adjusted to account for a shift between the first and second resonant center frequencies;
   g) wherein the bandstop filter comprises an overall circuit Q wherein the resultant 3 dB bandwidth is at least 10 kHz, such that the bandstop filter attenuates RF current flow substantially about the second resonant center frequency.

30. The lead of claim 29 wherein the second resonant center frequency comprises an MRI RF pulsed frequency.

31. The lead of claim 29 wherein the electromagnetic shield comprises an energy dissipating surface.

32. The lead of claim 29 wherein the electromagnetic shield is selected from the group consisting of a solid conductor, a wound spiral conductor, a mesh, a tubing, a nano-coating, a conductive heat-shrink. tubing, a conductive foil, a wire, a braid, a circuit trace, a solid tubular material, a conductive polymer, a conductive epoxy, a carbon nano-fiber, a nano-mesh, a nano-coating, and a nano-thread.

33. The lead of claim 29 wherein the inductance is formed by a discrete passive inductor.

34. The lead of claim 33 wherein the discrete passive inductor is selected from the group consisting of an inductor chip, an inductor winding, an inductor meander, a solenoid inductor, and an inductor trace.

35. The lead of claim 29 wherein the capacitance is formed by a discrete passive capacitor.

36. The lead of claim 35 wherein the discrete passive capacitor comprises a chip capacitor or a feedthrough capacitor.

37. The lead of claim 29 wherein the bandstop filter inductance comprises a coiled or spiral inductor, and the capacitance comprises a parasitic capacitance between adjacent turns of the coiled or spiral inductor and the capacitance comprises a parasitic capacitance between the turns of the coiled or spiral inductor and the shield.

38. The lead of claim 37 wherein the coiled or spiral inductor comprises a dielectric material, surrounding the coiled or spiral inductor.

39. The lead of claim 38 wherein the dielectric material has a dielectric constant greater than 1 up to 100.

40. The lead. of claim 29 wherein the shift between the first and second resonant center frequencies is greater than 3.0 mHz or 4.5%.

41. The lead of claim 29 including a torque carrier attached between the distal end of the conductor and the electrode, the torque carrier disposed mechanically in parallel to the bandstop filter, such that torque experienced by the electrode when inserted into the biological tissue is not transmitted to the bandstop filter.

42. An implantable lead, comprising:
   a) a conductor having a length extending from a proximal end to a distal end;
   b) a distal electrode contactable with biological cells disposed at the distal end of the conductor; and c) an LC circuit disposed in series along the length of the conductor, the LC circuit comprising a self resonant inductor having an inductance in parallel with a capacitance, wherein the LC circuit is shielded;
d) wherein the LC circuit comprises a first resonant center frequency when removed from the surrounding relationship with the electromagnetic shield and a second resonant. center frequency when in the surrounding relationship with the electromagnetic shield;
e) wherein the inductance or capacitance is adjusted to account for a shift between the first and second resonant frequencies;
f) wherein the LC circuit comprises an overall circuit Q wherein the resultant 3 dB bandwidth is at least 10 kHz, such that the LC circuit attenuates RF current flow substantially about the second resonant center frequency;
g) wherein the second resonant center frequency comprises an MRI RF pulsed frequency.

43. The lead of claim 42 wherein the LC circuit is disposed near, at or within the distal electrode.

44. The lead of claim 42 wherein the electromagnetic shield comprises an energy dissipating surface.

45. The lead of claim 42 wherein the electromagnetic shield comprises an open ended tubular or cylindrical shield.

46. The lead of claim 42 wherein the inductance is formed by a discrete passive inductor.

47. The lead of claim 46 wherein the discrete passive inductor is selected from the group consisting of an inductor chip, an inductor winding, an inductor meander, a solenoid inductor, and an inductor trace.

48. The lead of claim 42 wherein the capacitance is formed by a discrete passive capacitor.

49. The lead of claim 48 wherein the discrete passive capacitor comprises a chip capacitor or a feedthrough capacitor.

50. The lead of claim 42 wherein the LC circuit inductance comprises a coiled or spiral inductor, and the capacitance comprises a parasitic capacitance between adjacent turns of the coiled or spiral inductor.

51. The lead of claim 50 wherein the coiled or spiral inductor comprises a dielectric material surrounding the coiled or spiral inductor, such that adjacent turns of the coiled or spiral inductor are insulated from each other and the shield.

52. The lead of claim 51 wherein. the dielectric material has a dielectric constant greater than 1 up to 100.

53. The lead of claim 52 wherein the LC circuit inductance comprises a coiled or spiral inductor, and the capacitance comprises a parasitic capacitance between the turns of the coiled or spiral inductor and the shield.

* * * * *

UNITED STATES PATENT AND TRADEMARK OFFICE
CERTIFICATE OF CORRECTION

| | | |
|---|---|---|
| PATENT NO. | : 8,437,865 B2 | Page 1 of 1 |
| APPLICATION NO. | : 12/891292 | |
| DATED | : May 7, 2013 | |
| INVENTOR(S) | : Dabney et al. | |

It is certified that error appears in the above-identified patent and that said Letters Patent is hereby corrected as shown below:

On the Title page
Item [75], Inventors, delete "Mosciano" and insert --Moschiano--.

In the Claims:

Column 31, line 48 delete "RE" and insert --RF--.

Column 32, line 50 delete "material," and insert --material--.

Signed and Sealed this
Eighteenth Day of June, 2013

Teresa Stanek Rea
*Acting Director of the United States Patent and Trademark Office*